(12) United States Patent
Dumont et al.

(10) Patent No.: US 12,329,882 B2
(45) Date of Patent: Jun. 17, 2025

(54) ALIGNED HYDROGEL TUBES FOR TISSUE REPAIR AND REGENERATION

(71) Applicant: REGENTS OF THE UNIVERSITY OF MICHIGAN, Ann Arbor, MI (US)

(72) Inventors: Courtney M. Dumont, Ypsilanti, MI (US); Mitchell A. Carlson, Ann Arbor, MI (US); Lonnie D. Shea, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 980 days.

(21) Appl. No.: 17/050,876

(22) PCT Filed: Apr. 26, 2019

(86) PCT No.: PCT/US2019/029407
§ 371 (c)(1),
(2) Date: Oct. 27, 2020

(87) PCT Pub. No.: WO2019/210209
PCT Pub. Date: Oct. 31, 2019

(65) Prior Publication Data
US 2021/0322647 A1    Oct. 21, 2021

Related U.S. Application Data

(60) Provisional application No. 62/663,608, filed on Apr. 27, 2018.

(51) Int. Cl.
*A61L 27/52*   (2006.01)
*A61L 27/18*   (2006.01)
*A61L 27/56*   (2006.01)

(52) U.S. Cl.
CPC ............... *A61L 27/52* (2013.01); *A61L 27/18* (2013.01); *A61L 27/56* (2013.01); *A61L 2430/32* (2013.01)

(58) Field of Classification Search
CPC .......... A61L 27/52; A61L 27/18; A61L 27/56; A61L 2430/32; A61L 2300/252; A61L 2300/41; A61P 43/00
See application file for complete search history.

(56) References Cited

U.S. PATENT DOCUMENTS

| 7,427,602 B1 | 9/2008 | Shea et al. |
| 2008/0274161 A1 | 11/2008 | Muratoglu et al. |

(Continued)

FOREIGN PATENT DOCUMENTS

WO    WO-2016168669 A1 * 10/2016 ......... A61B 17/1128

OTHER PUBLICATIONS

Dumont et al., Controlled release strategies for modulating immune responses to promote tissue regeneration, J. Control Release, 219:155-166 (2015).

(Continued)

*Primary Examiner* — Christopher D. Prone
(74) *Attorney, Agent, or Firm* — MARSHALL, GERSTEIN & BORUN LLP

(57) ABSTRACT

Biomaterial implants and methods for facilitating tissue repair and regeneration are provided herein. The implants may include organized hydrogel structures. Such implants are fabricated using a 2-phase polymerization technique, wherein hydrogel-based microspheres are formed as an intermediate product of the 2-phase polymerization technique. The implants of various embodiments provide an aligned substrate to guide tissue regeneration and can be cut or formed to conform to the size and shape of an injury.

20 Claims, 10 Drawing Sheets
Specification includes a Sequence Listing.

(56) References Cited

U.S. PATENT DOCUMENTS

2010/0254900 A1* 10/2010 Campbell ............... A61P 29/00
424/9.4
2015/0084232 A1* 3/2015 Rutz ....................... A61L 27/18
435/325

OTHER PUBLICATIONS

Dumont et al., Neural stem cell-laden multichannel bridges support axon regeneration and neurogenesis following spinal cord injury. Submitted.

Dumont et al., Tissue Engineering Approaches to Modulate the Inflammatory Milieu following Spinal Cord Injury, Cells Tissues Organs., 202(1-2):52-66 (2016).

Fenn et al., IL-4 signaling drives a unique arginase+/IL-1β+ microglia phenotype and recruits macrophages to the inflammatory CNS: consequences of age-related deficits in IL-4Ra after traumatic spinal cord injury, J. Neurosci., 34(26):8904-8917 (2014).

Gelain et al., Transplantation of nanostructured composite scaffolds results in the regeneration of chronically injured spinal cords, ACS Nano., 5(1):227-236 (2011).

Griffin et al., Accelerated wound healing by injectable microporous gel scaffolds assembled from annealed building blocks, Nat. Mater., 14(7):737-744 (2015).

Gunther et al., Cell-seeded alginate hydrogel scaffolds promote directed linear axonal regeneration in the injured rat spinal cord, Acta. Biomater., 27:140-150 (2015).

Guo et al., Granulocyte colony-stimulating factor improves alternative activation of microglia under microenvironment of spinal cord injury, Neuroscience, 238:1-10 (2013).

Hamilton et al., Myeloid colony-stimulating factors as regulators of macrophage polarization, Front Immunol., 5:554 (2014).

Han et al., The collagen scaffold with collagen binding BDNF enhances functional recovery by facilitating peripheral nerve infiltrating and ingrowth in canine complete spinal cord transection, Spinal Cord., 52(12):867-873 (2014).

Hunt et al., Myelination of axons emerging from neural progenitor grafts after spinal cord injury, Exp. Neurol., 296:69-73 (2017).

Anderson et al., Facilitators and barriers to spinal cord injury clinical trial participation: multi-national perspective of people living with spinal cord injury, J. Neurotrauma., 33(5):493-499 (2016).

Assuncao-Silva et al., Hydrogels and cell based therapies in spinal cord injury regeneration, Stem. Cells Int., 2015:948040 (2015).

Basso et al., Graded histological and locomotor outcomes after spinal cord contusion using the NYU weight-drop device versus transection, Exp. Neurol., 139(2):244-256 (1996).

Bethea et al., Systemically administered interleukin-10 reduces tumor necrosis factor-alpha production and significantly improves functional recovery following traumatic spinal cord injury in rats, J. Neurotrauma., 16(10):851-863 (1999).

Cao et al., The application of nanofibrous scaffolds in neural tissue engineering, Adv. Drug Deliv. Rev., 61(12):1055-1064 (2009).

Chung et al., Numbers of axons in lateral and ventral funiculi of rat sacral spinal cord, J. Comp. Neurol., 214(1):72-78 (1983).

Chung et al., Propriospinal fibers in the rat, J. Comp. Neurol., 217(1):47-53 (1983).

Colello et al., The incorporation of growth factor and chondroitinase ABC into an electrospun scaffold to promote axon regrowth following spinal cord injury, J. Tissue Eng. Regen. Med., (2013).

Cregg et al., Functional regeneration beyond the glial scar, Exp. Neurol., 253:197-207 (2014).

Didangelos et al., Regulation of IL-10 by chondroitinase ABC promotes a distinct immune response following spinal cord injury, J. Neurosci., 34(49):16424-16432 (2014).

Donnelly et al., Inflammation and its role in neuroprotection, axonal regeneration and functional recovery after spinal cord injury, Exp. Neurol., 209(2):378-388 (2008).

International Application No. PCT/US19/29407, International Search Report and Written Opinion, mailed Aug. 29, 2019.

International Application No. PCT/US19/29407, International Preliminary Report on Patentability, mailed Nov. 5, 2020.

Karimi et al., Mechanical properties of the human spinal cord under the compressive loading, J. Chem. Neuroanat., 86:15-18 (2017).

Kubinova et al., SIKVAV-modified highly superporous PHEMA scaffolds with oriented pores for spinal cord injury repair, J. Tissue Eng. Regen. Med., 9(11):1298-1309 (2015).

Lee et al., Endogenous expression of interleukin-4 regulates macrophage activation and confines cavity formation after traumatic spinal cord injury, J. Neurosci. Res., 88(11):2409-2419 (2010).

Lee et al., The global map for traumatic spinal cord injury epidemiology: update 2011, global incidence rate, Spinal Cord., 52(2):110-116 (2014).

Liddelow et al., Neurotoxic reactive astrocytes are induced by activated microglia, Nature, 541:481-487 (2017).

Liu et al., Tissue-engineered regeneration of completely transected spinal cord using induced neural stem cells and gelatin-electrospun poly (lactide-co-glycolide)/polyethylene glycol scaffolds, PLoS One, 10(3):e0117709 (2015).

Madigan et al., Current tissue engineering and novel therapeutic approaches to axonal regeneration following spinal cord injury using polymer scaffolds, Respir Physiol. Neurobiol., 169(2):183-199 (2009).

Margul et al., Reducing neuroinflammation by delivery of IL-10 encoding lentivirus from multiple-channel bridges, Bioeng. Transl. Med., 1(2):136-148 (2016).

Mccreedy et al., Semi-automated counting of axon regeneration in poly(lactide co-glycolide) spinal cord bridges, J. Neurosci. Methods, 263:15-22 (2016).

Miller et al., Synergistic effects of physical and chemical guidance cues on neurite alignment and outgrowth on biodegradable polymer substrates, Tissue Eng., 8(3):367-378 (2002).

Mothe et al., Repair of the injured spinal cord by transplantation of neural stem cells in a hyaluronan-based hydrogel, Biomaterials, 34(15):3775-3783 (2013).

Oakland et al., The biomechanical response of spinal cord tissue to uniaxial loading, Proc. Inst. Mech. Eng. H., 220(4):489-492 (2006).

Ozawa et al., Comparison of spinal cord gray matter and white matter softness: measurement by pipette aspiration method, J. Neurosurg., 95:221-224 (2001).

Pawar et al., Biomaterial bridges enable regeneration and re-entry of corticospinal tract axons into the caudal spinal cord after SCI: Association with recovery of forelimb function, Biomaterials, 65:1-12 (2015).

Pomeshchik et al., Interleukin-33 treatment reduces secondary injury and improves functional recovery after contusion spinal cord injury, Brain Behav. Immun., 44:68-81 (2015).

Rajnicek et al., Contact guidance of CNS neurites on grooved quartz: influence of groove dimensions, neuronal age and cell type, J. Cell Sci., 110(Pt 23):2905-2913 (1997).

Shechter et al., Infiltrating blood-derived macrophages are vital cells playing an anti-inflammatory role in recovery from spinal cord injury in mice, PLoS Med., 6(7):e1000113 (2009).

Shikanov et al., Hydrogel network design using multifunctional macromers to coordinate tissue maturation in ovarian follicle culture, Biomaterials, 32(10):2524-2531 (2011).

Stirling et al., Depletion of Ly6G/Gr-1 leukocytes after spinal cord injury in mice alters wound healing and worsens neurological outcome, J. Neurosci., 29(3):753-764 (2009).

Thomas et al., Channel density and porosity of degradable bridging scaffolds on axon growth after spinal injury, Biomaterials, 34(9):2213-2220 (2013).

Tsai et al., Matrix inclusion within synthetic hydrogel guidance channels improves specific supraspinal and local axonal regeneration after complete spinal cord transection, Biomaterials, 27(3):519-533 (2006).

Tuinstra et al., Long-term characterization of axon regeneration and matrix changes using multiple channel bridges for spinal cord regeneration, Tissue Eng. Part A, 20(5-6):1027-1037 (2014).

Vannier et al., Coordinated antiinflammatory effects of interleukin 4: interleukin 4 suppresses interleukin 1 production but up-regulates

(56) References Cited

OTHER PUBLICATIONS gene expression and synthesis of interleukin 1 receptor antagonist, Proc. Natl. Acad. Sci. U.S.A., 89(9):4076-4080 (1992).
Zisch et al., Cell-demanded release of VEGF from synthetic, biointeractive cell ingrowth matrices for vascularized tissue growth, FASEB J., 17(15):2260-2262 (2003).

* cited by examiner

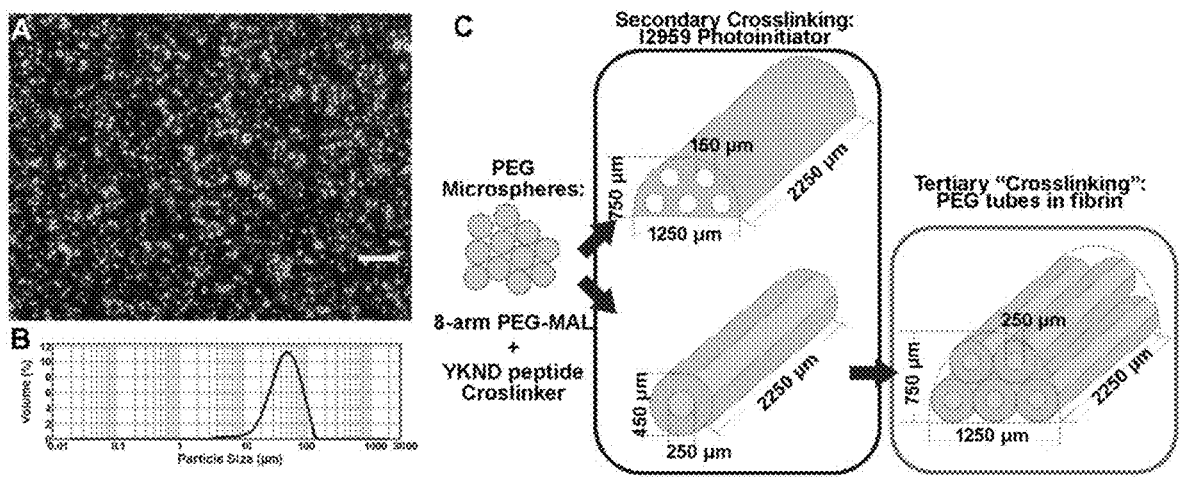

Figure 1. PEG-MAL microspheres are created with a water/oil emulsion method using a plasmin sensitive YKND peptide crosslinker (A). (B) Resulting microspheres had a diameter distribution ranging from 20-80 μm with an average size of 45 μm. (C) Tubes and bridges can be fabricated from the microspheres using UV-sensitive I2959 photoinitiator to crosslink remaining MAL side arms not crosslinked during microsphere fabrication. Tubes can be subsequently formed into a bridge composite using fibrin hydrogel to hold the tubes together for implantation. Scale bar 100 μm.

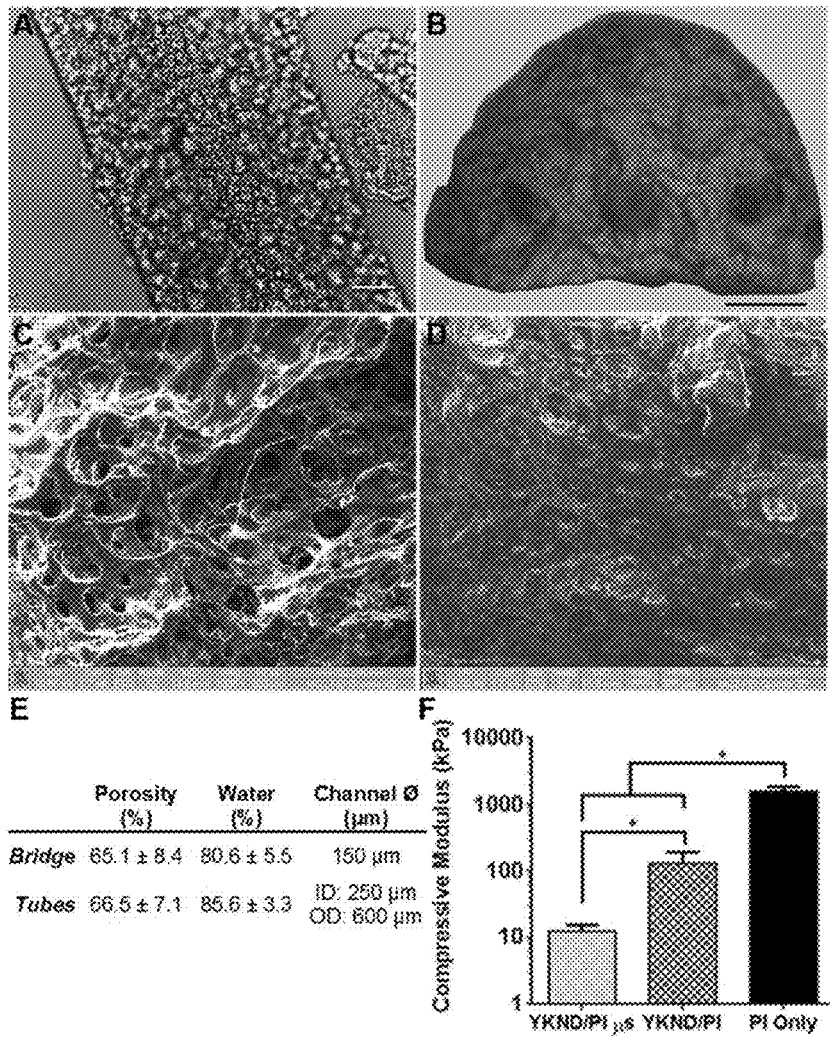

Figure 2. Tertiary structures, such as tubes and bridges can be created using a second crosslinking phase that capitalizes on MAL sidechains that were not utilized during microsphere fabrication. Resulting tubes (A, scale bar 100 μm) and bridges (B, scale bar 200 μm) generated from the PEG-MAL microspheres are porous and contain aligned channels within the material. Using SEM, pores can be seen through the hydrogel tubes (C) and bridges (D), albeit the pore structure does appear to vary between the two structures. (E) No significant differences in the porosity, swelling ratio, or water retention capacity were detected between the two structures. (F) Young's modulus was for PEG-MAL crosslinked with YKND/PI using microspheres (12.52 kPa) that was used to generate tubes and bridges was significantly lower ($p < 0.0001$) than the modulus for PEG-MAL crosslinked with YKND/PI without first forming microspheres (129.2 kPa) and PI only (1588 kPa).

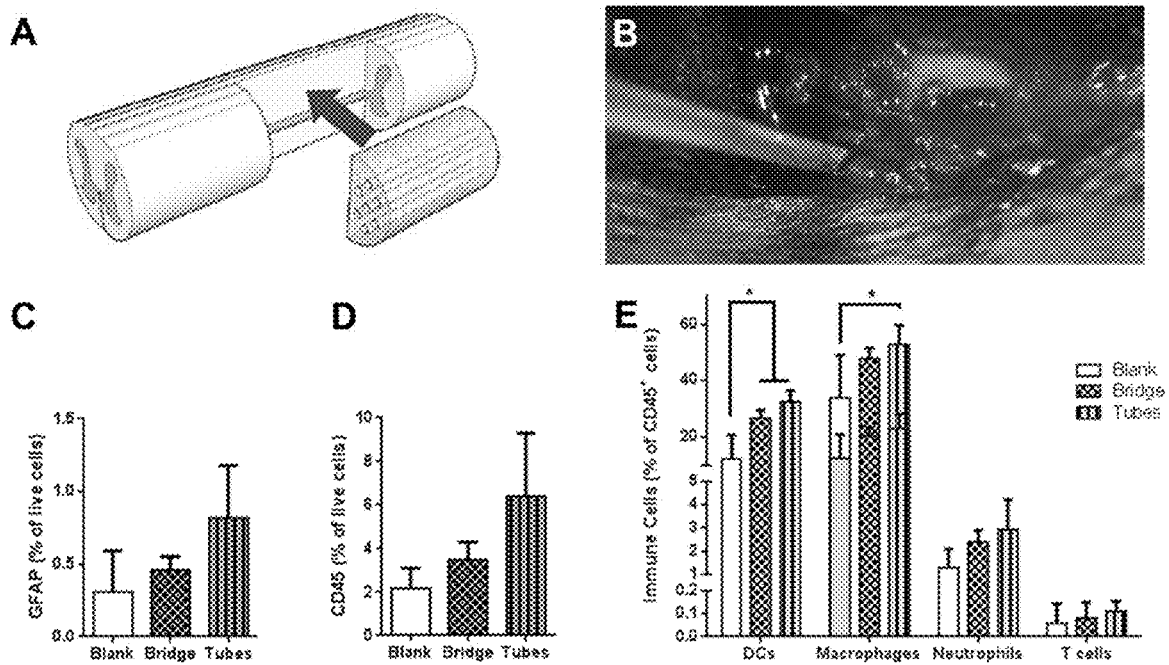

Figure 3. Immune cell infiltration 7 days after injury. Gelfoam, PEG bridges, or PEG tubes were implanted into a lateral hemisection spinal cord injury (A) and apposition to intact tissue was verified (B). GFAP$^+$ astrocytes (C) and CD45$^+$ leukocytes (D) infiltrate the injury site, however, no difference in the bulk populations of these cells are evident across the blank (gelfoam) injury or PEG scaffolds. (E) Further evaluation of the leukocyte phenotypes including CD11c$^+$ DCs, F4/80$^+$ macrophages, F4/80$^+$arginase$^+$ M2 macrophages (teal), Ly6g$^+$ neutrophils, and CD4$^+$ T-cells identified a significant increase in DCs and macrophages within the PEG materials. Data are represented as mean ± standard deviation. n = 5, * p < 0.05.

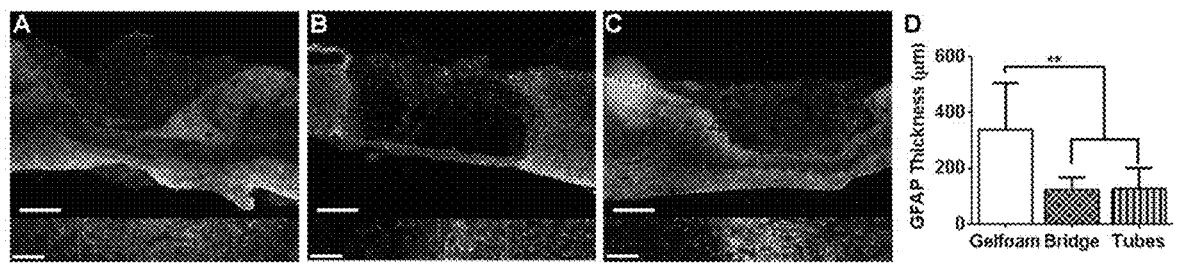

Figure 4. Glial scar thickness 14 days after injury. GFAP$^+$ astrocytes were observed throughout the intact tissue with robust staining at the interface of the gelfoam (A), bridge (B), and tube (C) implants with the intact tissue. The rostral margin thickness was measured at multiple locations for each tissue. (D) PEG implants significantly reduced glial scar thickness ($p < 0.01$) compared to the gelfoam control. Data are represented as mean ± standard deviation. n= 3, ** $p < 0.01$. 500 µm, 100 µm (inset) scale bars.

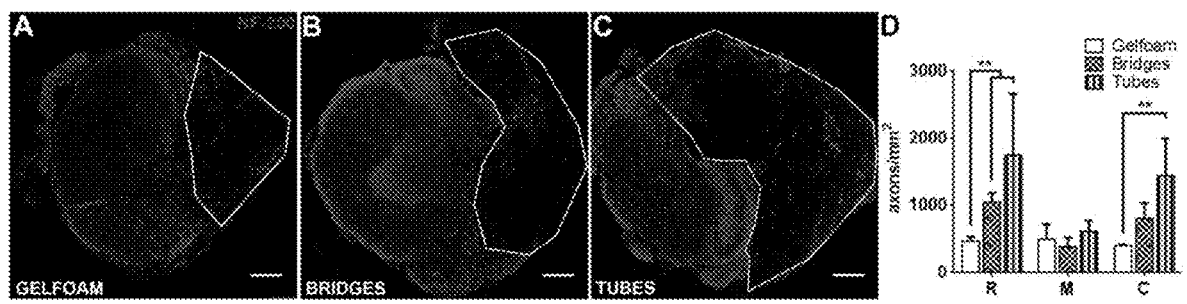

Figure 5. PEG implants enhance axon elongation at 8 weeks after transplantation in T9-10 hemisection. Qualitatively, NF-200$^+$ (red) axon expression is greater in PEG implants (A,B) compared to gelfoam (C). (D) Quantification of regenerating axons was binned into three 0.75 mm lateral sections of the bridge: R-rostral, M-middle of the injury, and C-caudal. Axon density is increased at both the rostral and caudal segments in mice receiving tubes composites, while only at the rostral margin for mice receiving hydrogel bridges compared to gelfoam at 8 weeks post injury. Data are represented as mean ± standard deviation . n = 6, ** $p < 0.01$. 200 μm scale bar.

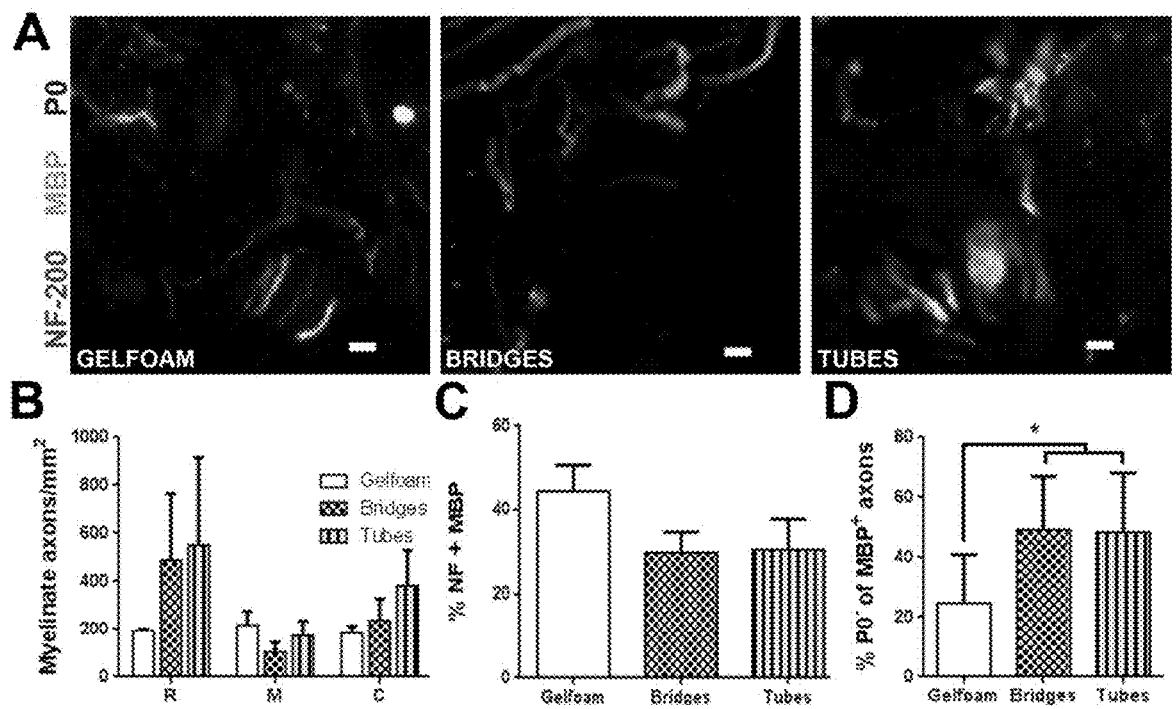

Figure 6. Axon myelination is supported in all conditions at 8 weeks post injury. (A)NF-200+ axons co-localized with oligodendrocyte derived myelin (MBP+; green) and with Schwann cell myelin (MBP+, P0+; blue) within transverse sections of the bridge across all conditions. No significant difference was observed in the density (B) or percentage (C) of total myelinated axons, independent of myelinating cell source. (D) Both PEG tubes and bridges did result in a significant increase in the percentage of oligodendrocyte-derived myelin (NF-200+MBP+P0-; $p < 0.05$) compared to gelfoam. Data are represented as mean ± standard deviation . n = 6, * $p < 0.05$. 10 μm scale bar.

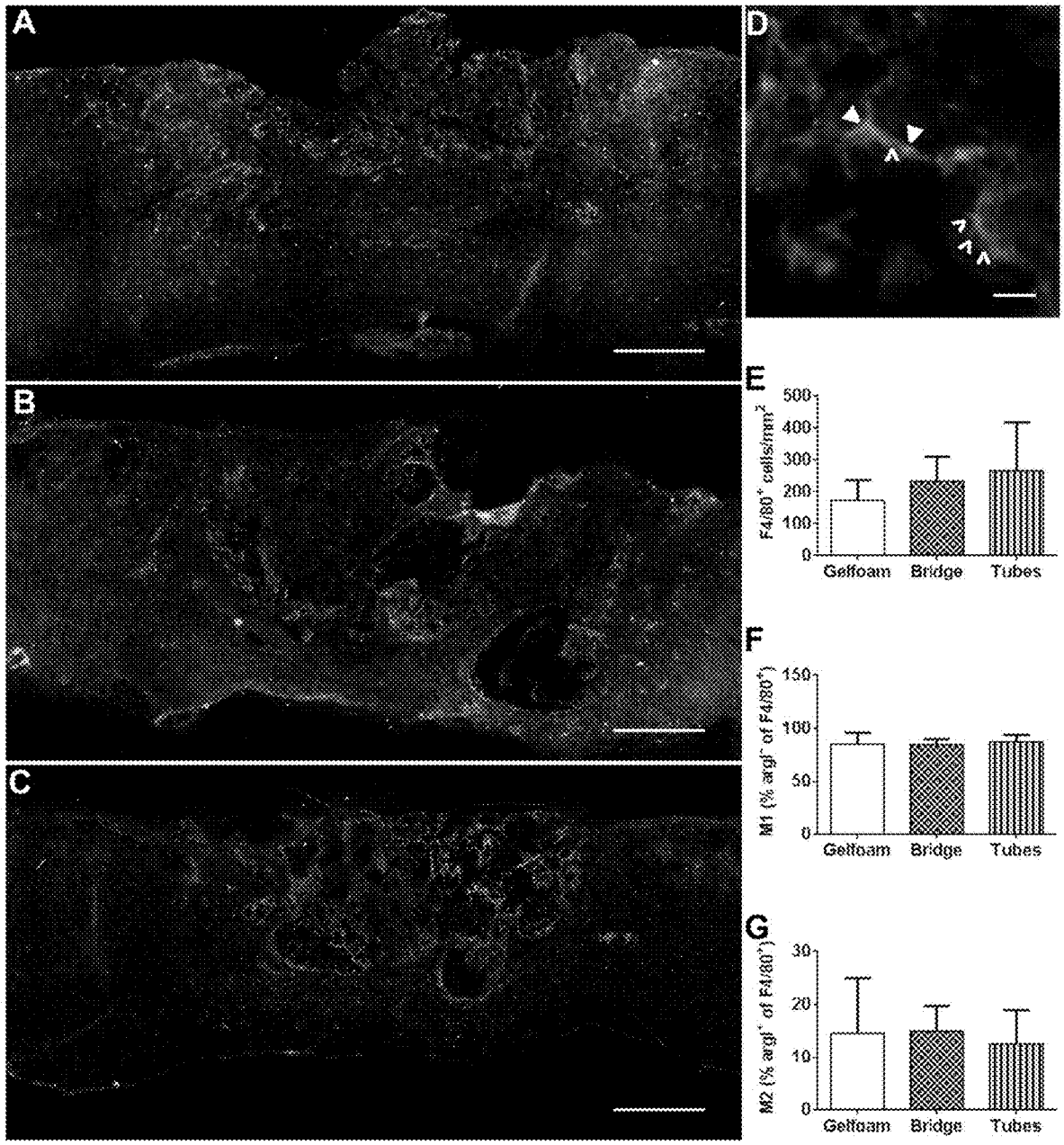

Figure 7. Macrophages are within the injury and surround tissue two weeks after injury. Cells nuclei (Hoechst, blue) are observed throughout the tissue for mice receiving gelfoam (A), PEG bridges (B), and PEG tubes (C) with intense staining along the interface of the injured tissue and implants. A subset of these cells F4/80$^+$ macrophages (red), which were quantified as M1 (F4/80$^+$argI$^-$, red, denoted with arrow head) or M2 (F4/80$^+$argI$^+$, red + green, denoted with >) macrophages when co-localized with nucleus (D). Total macrophage density (E) as well as the percent of macrophages that were M1 (F) or M2 (G) phenotypes were quantified and no significant differences were observed across the three implant conditions. Data are represented as mean ± standard deviation. n = 3, 500 μm scale bar.

ered as prior art against the present disclosure.

SEQUENCE LISTING

```
<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 1

Lys Gln Ala Gly Asp Val
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2

Val Ala Pro Gly
1

<210> SEQ ID NO 3
<211> LENGTH: 20
<212> TYPE: PRT
```

```
<213> ORGANISM: Artificial Sequence
<220> FEATURE:
<223> OTHER INFORMATION: Synthetic Peptide

<400> SEQUENCE: 3

Tyr Ser Phe Asn Tyr Asp Gly Ser Glu Leu Ile Ile Lys Lys Val Asp
1               5                   10                  15

Lys Ser Asp Glu
            20

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Ala Ser Lys Lys Pro Lys Arg Asn Ile Lys Ala
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Tyr Lys Asn Asp
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

Tyr Lys Asn Ser
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 7

Tyr Lys Asn Arg
1

<210> SEQ ID NO 8
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 8

Gly Lys Cys Asp Gly Pro Gln Gly Tyr Ile Trp Gly Gln Asp Cys Lys
1               5                   10                  15

Gly
```

```
<210> SEQ ID NO 9
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 9

Gly Cys Arg Asp Gly Pro Gln Gly Ile Trp Gly Gln Asp Arg Cys Gly
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 10

Gly Cys Tyr Lys Asn Asp Gly Cys Tyr Lys Asn Asp Cys Gly
1               5                   10
```

ALIGNED HYDROGEL TUBES FOR TISSUE REPAIR AND REGENERATION

CROSS-REFERENCE TO RELATED APPLICATIONS

This application is the U.S. national phase of PCT Application No. PCT/US19/29407, filed on Apr. 26, 2019, which claims the benefit of U.S. Provisional Application No. 62/663,608, filed on Apr. 27, 2018, the disclosures of which are incorporated herein by reference.

STATEMENT OF GOVERNMENT SUPPORT

This invention was made with government support under grant number EB005678 awarded by the National Institutes of Health. The government has certain rights in the invention.

FIELD OF THE DISCLOSURE

The present disclosure relates generally to biomaterial implants and, more particularly, to biomaterial implants and techniques for facilitating tissue repair and regeneration.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Many tissue engineering applications require a material that can conform to any defect size while supporting direct growth. Hydrogels are favored for their ability to conform to the injury site, but do not provide topographical cues to support regeneration. Conversely, rigid scaffolds with aligned channels or fibers support and guide regrowth, but do not readily conform to the injury geometries.

SUMMARY OF THE INVENTION

Numerous scaffolds have previously been developed in an effort to support repair and regeneration after spinal cord injury; however, many of these scaffolds have only addressed nerve guidance (bridges) or variable defect geometries (hydrogels) and are incapable of doing both. Accordingly, a need exists for improved tissue repair and regeneration devices, systems, and methods.

The present disclosure is generally directed to biomaterial implants comprising organized hydrogel structures, such as a porous hydrogel tube and/or aligned hydrogel tubes and/or bridge structures, and related systems and methods for facilitating tissue repair and regeneration. A highly porous hydrogel structure is disclosed herein, which consists of, consists essentially of, or comprises two or more tubes that can conform to any defect size and provide an aligned substrate to guide tissue (e.g., axon, nerve, and/or cell) regeneration. In various embodiments, the two or more tubes couple together to form a tube system or tube composite. The tube composite can be formed at the site of injury, creating a personally-tailored, injury-specific modular bridge, with the number and length of tubes modified to fit nearly any injury.

Various embodiments provided herein combine the therapeutically beneficial aspects of bridges and hydrogels into a singular treatment option that has the potential for increased utility in the treatment of spinal cord injuries, as well as broader applications in other nerve, musculoskeletal, and cardiovascular repair models.

One aspect of the disclosure provides a method of manufacturing an organized hydrogel structure, the method comprising providing a plurality of hydrogel particles, and cross-linking the plurality of hydrogel particles to form the organized hydrogel structure, wherein (a) the plurality of hydrogel particles are provided in a mold having the organized hydrogel structure or (b) the cross-linking step occurs prior to or concurrently with extruding or printing the plurality of hydrogel particles into the organized hydrogel structure.

Another aspect of the disclosure provides a porous hydrogel tube comprising a plurality of hydrogel particles, wherein the hydrogel particles are cross-linked to each other in the form of a tube.

Another aspect of the disclosure provides a scaffold for tissue repair, comprising two or more porous hydrogel tubes according to the disclosure.

Another aspect of the disclosure provides a method of regenerating tissue comprising implanting in an injury site an implant comprising two or more porous hydrogel tubes according to the disclosure, wherein the hydrogel tubes are aligned and stacked within the injury site.

BRIEF DESCRIPTION OF THE DRAWINGS

FIG. 1 depicts: (A) a photograph of PEG-MAL microspheres created with a water/oil emulsion method using a plasmin sensitive YKND(SEQ ID NO: 5) peptide cross-linker; (B) a graph of the diameter distribution of the resulting microspheres; and (C) a schematic depiction of one method of fabricating aligned hydrogel tubes from the PEG-MAL microspheres.

FIG. 2 depicts: (A) a photograph of hydrogel tubes (scale bar=100 μm) generated from PEG-MAL microspheres; (B) a photograph of hydrogel bridges (scale bar=200 μm) generated from PEG-MAL microspheres; (C) an SEM image of the pores of the hydrogel tubes of (A); (D) an SEM image of the pores of the hydrogel bridges of (B); (E) a table of the porosity, swelling ratio, and channel diameter of the tubes of (A) and bridges of (B); and (F) a graph comparing: (i) the Young's modulus for the PEG-MAL cross-linked with YKND(SEQ ID NO: 5)/PI using microspheres (which was used to generate the tubes and bridges) to (ii) the modulus for PEG-MAL cross-linked with YKND(SEQ ID NO: 5)/PI without first forming microspheres and to (iii) the modulus for PI only.

FIG. 3 depicts: (A) a schematic of a lateral hemisection spinal cord injury with an implant of the present disclosure being inserted into the injury site; (B) a photograph of a lateral hemisection spinal cord injury with an implant of the present disclosure in the injury site, wherein the implant is in contact with (i.e., apposition to) adjacent intact tissue; (C) a chart comparing the amount of GFAP$^+$ astrocytes that infiltrated the injury site; (D) a chart comparing the amount of CD45$^+$ leukocytes that infiltrated the injury site; and (E) a chart comparing the bulk populations of dendritic cells, macrophages, neutrophils, and T-cells that infiltrated the injury site.

FIG. 4 depicts: (A) a side view of a gelfoam control implanted into a hemisection spinal cord injury, and an associated glial scar thickness; (B) a side view of a bridge of the present disclosure implanted into a hemisection spinal cord injury, and an associated glial scar thickness; (C) a side view of a modular tube device of the present disclosure implanted into a hemisection spinal cord injury, and an associated glial scar thickness; and (D) a graph comparing the glial scar thickness of (A), (B), and (C).

FIG. 5 depicts: (A) a cross-sectional view of a gelfoam control implanted into a hemisection spinal cord injury, the image stained with NF-200+ to depict axon expression; (B) a cross-sectional view of a bridge of the present disclosure implanted into a hemisection spinal cord injury, the image stained with NF-200+ to depict axon expression; (C) a cross-sectional view of a modular tube device of the present disclosure implanted into a hemisection spinal cord injury, the image stained with NF-200+ to depict axon expression; and (D) a graph comparing the axon density of the rostral, middle, and caudal portions of the implants of (A), (B), and (C).

FIG. 6 depicts: (A) stained images of a gelfoam control, a bridge of the present disclosure, and a modular tube device of the present disclosure; (B) a graph comparing the axon density of the rostral, middle, and caudal portions of the implants of (A); (C) a graph comparing the percentage of total myelinated axons observed in the implants of (A); and (D) a graph comparing the percentage of oligodendrocyte-derived myelin observed in the implants of (A).

FIG. 7 depicts: (A) a perspective view of a gelfoam control implanted into a hemisection spinal cord injury, the image stained to highlight cell nuclei and associated cell growth in the implant; (B) a perspective view of a bridge of the present disclosure implanted into a hemisection spinal cord injury, the image stained to highlight cell nuclei and associated cell growth in the implant; (C) a perspective view of a modular tube device of the present disclosure implanted into a hemisection spinal cord injury, the image stained to highlight cell nuclei and associated cell growth in the implant; (D) a magnification of the stained images showing F4/80+ macrophages (denoted with arrow head) and F4/80+ argI+ (denoted with >); (E) a graph comparing the total macrophage density of the implants of (A), (B), and (C); (F) a graph comparing the percent of macrophages that were M1 in the implants of (A), (B), and (C); and (G) a graph comparing the percent of macrophages that were M2 in the implants of (A), (B), and (C).

DETAILED DESCRIPTION

Figure 8:
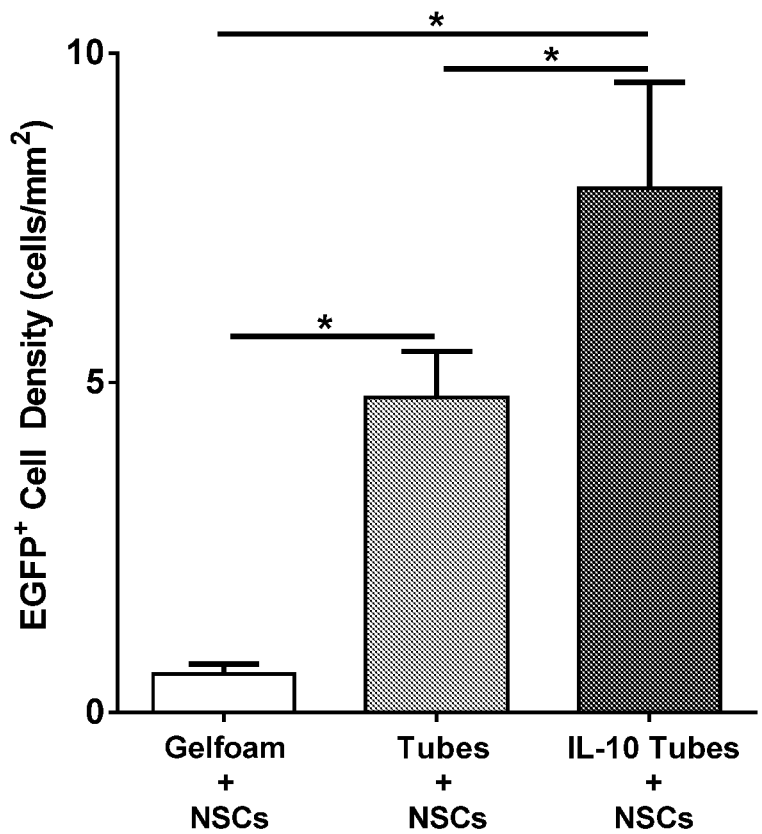
FIG. 8 is a graph comparing the EGFP+ cell density for mice implanted with gelfoam, hydrogel tubes, and anti-inflammatory loaded hydrogel tubes, and injected with EGFP+ NSCs. EGFP+ density is reported 2 weeks after NSC implantation and is representative of increased NSC transplant survival.

The present disclosure is generally directed to organized hydrogel structures for use as biomaterial implants such as a porous hydrogel tube, aligned hydrogel tubes, or bridge structures and related systems and methods for facilitating tissue repair and regeneration. A highly porous hydrogel is disclosed herein, which consists of, consists essentially of, or comprises two or more tubes that can conform to any defect size and provide an aligned substrate to guide tissue (e.g., axon, nerve, and/or cell) regeneration. In various embodiments, the two or more tubes couple together to form a tube system or tube composite. The tube composite can be formed at the site of injury, creating a personally-tailored, injury-specific modular bridge, with the number and length of tubes modified to fit nearly any injury.

The organized hydrogel structures of the disclosure comprise hydrogel particles. The organized hydrogel structures can be secondary structures, e.g., organized hydrogel particles, or tertiary or higher structures, e.g., organized and/or modular secondary structures. Secondary structures can include, but are not limited to, porous hydrogel tubes or porous hydrogel bridge structures. In general, secondary structures are prepared as a single structure using a mold, extruder, or 3D printer. Tertiary structures can include tube systems or tube composites, e.g., a modular bridge structure comprising two or more porous hydrogel tubes. In general, tertiary structures are prepared in a modular fashion (i.e., from two or more individually manufactured secondary structures). As used herein, and unless specified otherwise, "tube systems" and "tube composites" are interchangeable terms. As used herein, and unless specified otherwise, a "bridge structure" refers to a multi-channel structure provided in a bridge shape, e.g., for a hemisection, having a flat edge and a rounded edge, as shown in, for example, FIG. 2B or for a full cross-section, having a full oval shape. While the bridge structure in FIG. 2B is a 5-channel bridge, it will be appreciated that the number of channels is not limited to 5, but can be any number, for example, in a range of about 2 to about 100, for example, 2, 3, 4, 5, 6, 7, 8, 9, 10, 15, 20, 25, 30, 40, 50, 60, 70, 80, 90, or 100. Further, depending on the size of the injury, multiple bridge structures having from 5 to 20 channels, for example, can be used together to fill the injury site.

As used herein, and unless specified otherwise, the term "tube" encompasses any structure having a first end and a second end distal from the first end, a length spanning from the first end and the second end, and a lumen running the length of the structure from the first end to the second end. As used herein, and unless specified otherwise, the terms "lumen" and "channel" are used interchangeably. Accordingly, a tube can have any cross-sectional shape, including but not limited to circular (e.g., a straw-like structure), square, star shaped, and any combination thereof. Tertiary structures of cross-linked star shaped tubes can be advantageous for tissue regeneration as the arms of the stars create void spaces between individual star tubes, thereby providing additional directionally aligned channels for promoting guided tissue regeneration, for example. As used herein and unless specified otherwise, two or more channels or lumens are "aligned" if flow through each individual channel or lumen (e.g., blood flow) or cell growth in each individual channel or lumen is guided from a first site to a second site, without significant deviation.

In some embodiments provided herein, the devices, systems, and methods are described with reference to spinal cord repair; however, it will be appreciated by those skilled in the art that the embodiments described herein can be used for the repair of any tissue that requires cellular alignment, including, but not limited to, vascular tissue and muscle.

Nearly a quarter million individuals worldwide incur spinal cord injuries each year, resulting in loss of function in tissues below the level of spinal injury. Trauma to the spinal cord can present as either contusive or penetrating injuries, with neither injury model having viable clinical treatment options to repair the damaged tissue and restore function. While both injury models undergo extensive inflammation, there are nuances in the infiltration and extent of inflammation associated with each model that hinder regeneration and functional recovery. For this reason, the primary focus and measurement of success is to promote axons extending into and through the injury and synapsing onto intact distal targets. A number of biomaterials have been used to support axon extension by filling the void left after injury. Penetrating injuries benefit from a bridge that both fills the injury site and guides re-growing axons and infiltrating support cells. Contusion injuries may not readily exhibit large tissue defects that can support bridge implantation, and instead rely heavily on injectable materials that offer a substrate for attachment but do not provide axonal guidance.

Regeneration of structurally organized tissues benefits from physical guidance systems to ensure proper organization of repaired tissues. The spinal cord is a highly organized structure, predominantly with rostral-caudal alignment of axons and myelin making it an ideal tissue for evaluating aligned bridges. Previous work using multi-channel bridges has shown directed axon elongation and can achieve half of the axon density as the intact contralateral tissue by 6 months. The prior art bridges have a high degree of porosity, allowing for infiltration of progenitors that differentiate into the myelinating oligodendrocytes resulting in 30% of the axons being myelinated by 8 weeks and up to 40% by 6 months. By comparison, 40-60% of healthy spinal cord axons are myelinated. While the prior art bridges have been demonstrated to hold great promise, they are preformed into a desired shape prior to implantation and cannot be easily modified, thus limiting the applicability. Moreover, previous bridges have addressed the issue of topographical guidance, but other biophysical cues, namely modulus and viscoelastic properties, have not been designed to match that of the spinal cord. Looking to other classes of biomaterials may help to address these deficits and expand the utility to both penetrating and contusive injuries.

Hydrogels can conform to any defect size or shape, thus making them an attractive alternative to promote nerve regeneration in the spinal cord. Current hydrogel strategies inject a solution that can polymerize in situ, conforming to the shape of the defect. Depending on the design of the hydrogel system implemented, the gels may swell in the aqueous in vivo environment after injection. If the hydrogels have not been polymerized and allowed to swell prior to implantation, then the swelling of the gel in the in vivo environment may lead to further compressive injury which needs to be considered during the design process. Hydrogels can be designed to match appropriate biophysical cues (modulus, viscoelasticity, porosity, etc.), yet they lack topographical cues that have been shown to guide re-growing axons, thus limiting their effectiveness at regeneration, particularly in large gap defects.

Existing scaffolds have generally only addressed nerve guidance (bridges) or variable defect geometries (hydrogels) but are incapable of doing both. Accordingly, in some aspects of the present disclosure, an improved implant is described, which combines the therapeutically beneficial aspects of bridges and hydrogels into a singular treatment option that has the potential for increased utility in the treatment of spinal cord injuries, as well as broader applications in other nerve, musculoskeletal, or cardiovascular repair models.

In some aspects of the present disclosure, modular tube systems and hydrogel-based multi-channel bridges are described, which are fabricated using a 2-phase polymerization technique. In some aspects of the present disclosure, a method of fabricating aligned hydrogel tube systems and multi-channel bridges is described. In some aspects of the present disclosure, a method of implanting aligned hydrogel tube systems and multi-channel bridges is described.

Hydrogel Particles

The organized hydrogel structures of the disclosure comprise a plurality of hydrogel particles. In embodiments, the plurality of hydrogel particles comprises a PEG-based material, collagen, alginate, hyaluronic acid, chitosan, methylcellulose, or a combination thereof. In embodiments, the plurality of hydrogel particles comprises a PEG-based material, collagen, alginate, or a combination thereof.

As used herein, "PEG" refers to polyethylene glycol. A "PEG-based material" refers to a material comprising a polyethylene glycol backbone. "Average molecular weight" is given its ordinary and accustomed meaning of the arithmetic mean of the molecular weights of the components (e.g., molecules) of a composition, regardless of the accuracy of the determination of that mean. For example, polyethylene glycol, or PEG, having an average molecular weight of 3.5 kilodaltons may contain PEG molecules of varying molecular weight, provided that the arithmetic mean of those molecular weights is determined to be 3.5 kilodaltons at some level of accuracy, which may reflect an estimate of the arithmetic mean, as would be understood in the art. Any PEG is contemplated for use in the compositions and methods of the disclosure. In general, the PEG has an average molecular weight of at least about 5,000 daltons. In further embodiments, the PEG has an average molecular weight of at least or at least about 10,000 daltons, 15,000 daltons, 20,000 daltons, 25,000 daltons, 30,000 daltons, for example between 10,000 and 30,000 daltons, or between 15,000 and 20,000 daltons. In embodiments, the PEG can have an average molecular weight of 5,000, of 6,000, of 7,000, of 8,000, of 9,000, of 10,000, of 11,000, of 12,000 of 13,000, of 14,000, 15,000, 20,000, 25,000, or of 30,000 daltons or more.

The polyethylene glycol backbone can be modified or non-modified. A PEG backbone can be modified to introduce reactive side arms onto the backbone of the PEG material. As used herein, "reactive side arms" refer to functional groups on the backbone of a hydrogel material which can facilitate intra- and inter-particle crosslinking and/or direct conjugation of relevant factors onto the material. Reactive side arms suitable for use with PEG-based materials include, but are not limited to, maleimide (MAL) modified, acrylate (Ac) modified, vinyl sulfone (VS) modified and/or any thiol-containing side arm. In embodiments, the reactive side arm for use with PEG-based materials comprise, maleimide, acrylate, vinyl sulfone, or a combination thereof. In various embodiments, the PEG is a four-arm PEG or an eight-arm PEG. In some embodiments, the PEG-based material comprises 4-arm PEG maleimide (4-arm PEG-MAL), 8-arm PEG-MAL, 4 arm PEG-acrylate (4-arm PEG-Ac), 8 arm PEG-Ac, 4 arm PEG-vinyl sulfone (4-arm PEG-VS), 8 arm PEG-VS, or a combination thereof. In embodiments, the PEG-based material comprises 8-arm PEG MAL.

In embodiments, the hydrogel material comprises a material other than PEG. Suitable hydrogel materials other than PEG include, but are not limited to, collagen, alginate, hyaluronic acid, chitosan, methylcellulose, or a combination thereof. In embodiments, the hydrogel material other than PEG include reactive side arms.

Advantageously, the hydrogel material can be selected to tune one or more properties of the hydrogel material, including, but not limited to, mechanical strength, pore size, and functionality of the resulting structure, including primary functionality (e.g., cellular guidance and/or filling defect geometries) and/or secondary functionality (e.g., drug delivery, or reduction/prevention of inflammation).

The hydrogel particles can be made using any method known in the art. For example, oil/water emulsion methods, microfluidic fabrication methods, lithography, or 3D printed droplet techniques. The resulting particles can be cross-linked to form stable hydrogel particles. For example, the hydrogel materials of the hydrogel particles can be cross-linked by Michael type addition with Plasmin sensitive peptide or MMP sensitive peptide, or by calcium chloride cross-linking. Methods of cross-linking hydrogels to form stable particles are well known in the art.

In embodiments, the hydrogel particles are spherical. The hydrogel particles can have a particle diameter in a range of about 1 to about 200 µm, about 5 to about 150 µm, about 10 to about 125 µm, about 15 to about 100 µm, or about 20 to about 80 µm. The particle diameter of the plurality of hydrogel particles can be homogeneous, e.g., having a size distribution range of about 10 µm, or heterogeneous, e.g., having a size distribution range of greater than 50 µm, greater than 60 µm, greater than 70 µm, greater than 80 µm, greater than 90 µm, or greater than 100 µm, for example.

Organized Hydrogel Structures

The plurality of hydrogel particles can be organized into secondary scaffold structures, such as a porous hydrogel tube or a porous multi-channel bridge structure. Two or more porous hydrogel tubes can be organized into a tertiary scaffold structure, such as a bridge configuration. The term "scaffold," as used herein, refers to a means of physical support for use in tissue engineering or tissue regeneration. Scaffolds of the present disclosure may comprise any of a large variety of structures including, but not limited to, particles, beads, polymers, surfaces, implants, matrices, etc. Scaffolds may be of any suitable shape, for example, spherical, generally spherical (e.g., all dimensions within 25% of spherical), ellipsoidal, rod-shaped, globular, polyhedral, etc. The scaffold may also be of an irregular or branched shape. In embodiments, the organized hydrogel structure comprises a tube, a bridge, or a combination thereof.

In general, porous secondary structures can be prepared by cross-linking a plurality of hydrogel particles together. The porous organized hydrogel structures can be prepared by cross-linking in a mold having the desired organized structure and/or cross-linking prior to or concurrently with extruding or printing the plurality of hydrogel particles into the organized hydrogel structure. The void space between individual hydrogel particles provides the porosity in the secondary structure. In general, the secondary structure will have a channel or lumen spanning from a first end of the secondary structure to a second end of the secondary structure, for example, to promote cellular alignment in an injury site.

Hydrogel microparticles can be cross-linked together to form secondary, porous organized hydrogel structures using any known method in the art. In embodiments, the cross-linking of the plurality of hydrogel particles comprises irradiating the plurality of hydrogel particles with UV/VIS light, chemical cross-linking, thermal cross-linking, pH responsive cross-linking, or a combination thereof. In embodiments, the cross-linking of the plurality of hydrogel particles comprises irradiating the plurality of hydrogel particles with ultraviolet (UV) or visible spectra (VIS) light. In refinement of the foregoing embodiment, the plurality of hydrogel particles which are irradiated with UV or visible spectra light further comprise a photo initiator. Photo initiators are generally known in the art and can include, but are not limited to, acetophenone derivatives (e.g. Igracure 2959), benzoin derivatives, benziketals, hydroxyalkylphenones, camphorquinone, phenylpropanedione, monoacrylphosphine oxide (TPO), and bisacrylphosphine oxide (Ir819). As will be understood by one of ordinary skill, the photo initiator can be selected to respond to a particular wavelength of light in the ultra violet region of the electromagnetic spectrum.

In embodiments, the cross-linking of the plurality of hydrogel particles comprises chemical cross-linking. Methods of chemical cross-linking are known in the art. For example, chemical cross-linking can include contacting the plurality of hydrogel particles with a cross-linking agent such as glutaraldehyde and/or epichlorohydrin. Chemical crosslinking with glutaraldehyde and/or epichlorohydrin can be particularly advantageous when the hydrogel particles comprise hydrogels that include proteins, such as collagen and/or gelatin. Other non-limiting examples of chemical cross-linking include Michael type addition with Plasmin sensitive peptides (e.g., YKND(SEQ ID NO: 5), YKNS (SEQ ID NO: 6), YKNR(SEQ ID NO: 7)), and Michael type addition with metalo-matrix proteinase (MMP) sensitive peptides (e.g., GKCDGPQGYIWGQDCKG(SEQ ID NO: 8), GCRDGPQGIWGQDRCG (SEQ ID NO: 9)).

The pore size of the porous secondary structures is not particularly limited. In general, the pore size of the porous secondary structure is controlled by the particle size of the individual hydrogel particles that make up the secondary structure. Without intending to be bound by theory, it is believed that the pore size can be selected to facilitate a particular response (e.g., cell adhesion/seeding, cell migration, and/or cell proliferation) when the secondary structure is provided in an injury site. For example, the porous organized hydrogel structure can have a pore size in a range of about 10 µm to about 200 µm, about 10 µm to about 150 µm, about 10 µm to about 100 µm, about 10 µm to about 75 µm, about 10 µm to about 50 µm, about 25 µm to about 75 µm, about 25 µm to about 100 µm, about 25 µm to about 150 µm, about 50 µm to about 125 µm, about 60 µm to about 110 µm, or about 75 µm to about 200 µm. In particular, to facilitate growth and proliferation of anti-inflammatory macrophages, for example, a pore size in a range of about 30-40 µm can be selected to reduce the risk of formation of a foreign giant body cell. For endothelial cells, 30-40 µm promotes migration and proliferation into the graft, resulting in new vessel formation. In general, the larger the pore size, the softer the hydrogel structure and the more difficult handling of the structure will be.

Without intending to be bound by theory, it is believed that the mechanical strength/modulus of the organized hydrogel structure is controlled by the amount of cross-linking and void space between the individual hydrogel particles to form the secondary structure and between the secondary structures to form the tertiary structure. As shown in FIG. 2F, the compressive modulus of the cross-linked hydrogel structures (YKND(SEQ ID NO: 5)/PI μs (12.52 kPa) and YKND(SEQ ID NO: 5)/PI (129.2 kPa)) were lower than the compressive modulus of non-cross-linked hydrogel structures (PI only (1588 kPa)) and, further, the compressive modulus of the porous cross-linked hydrogel structures (prepared from cross-linked microspheres) was significantly lower than the modulus for the non-porous cross-linked hydrogel structures (formed by cross-linking a bulk gel with both cross-linking steps, rather than using a microsphere intermediary structure). In particular, it is believed that as the amount of crosslinking increases, the modulus of the resulting structure increases, although the extent of the change in modulus can also be affected by the method of crosslinking (e.g., Michael type vs. UV or VIS cross-linking vs. thermoresponsive). The amount of inter-particle cross-linking and inter-secondary structure cross-linking can be modified by modifying the amount of reactive side arms provided on the hydrogel materials and the conditions under which the cross-linking occurs. Another consideration for modifying the amount of cross-linking include the amount of liquid provided with the hydrogel particles (for example, the more liquid that is present, the further apart the individual particles are and fewer cross-links can form).

Without intending to be bound by theory, it is believed that as the number of reactive side arms on the hydrogel material increases, the number of free, non-cross-linked, side arms remaining after primary cross-linking (of the individual particles) increases when cross-linked under identical conditions, allowing for secondary cross-linking into secondary and/or tertiary structures and/or functionalization of the organized structures, e.g., with a drug or anti-inflammatory protein.

In embodiments, the plurality of hydrogel particles are provided in a mold having the organized hydrogel structure and then cross-linked to provide a stable secondary organized hydrogel structure. In alternative embodiments, the cross-linking step occurs prior to or concurrently with extruding or printing the plurality of hydrogel particles into the organized hydrogel structure. Extruding can comprise extruding the material from a syringe, extruder, or other suitable device. In embodiments, the extruding device has a pin-like structure in the center of the extruding orifice, thereby forming an individual porous hydrogel tube. Printing can comprise 3D printing of hydrogel particles and/or stereolithography. Stereolithography can be used to print hydrogel particles with increased resolution. The dual phase cross-linking process advantageously ensures that the hydrogel tubes are porous to facilitate tissue integration and that the tubes contain a central channel that supports uniaxial tissue growth, a feature that is essential for regeneration in highly structured tissues.

In embodiments, the organized hydrogel structure comprises a scaffold configured to promote cellular alignment in an injury site. As used here, a scaffold is configured to promote cellular alignment in an injury site if the scaffold contains a patterned void space to facilitate rapid cell infiltration, particularly infiltration from cells with limited remodeling capabilities (e.g., neurons). The void space can be a tube lumen, the outer surface of tube, or lumens formed between interfacing tubes.

Porous Hydrogel Tube

Another aspect of the disclosure provides a porous hydrogel tube comprising a plurality of hydrogel particles, wherein the hydrogel particles are cross-linked to each other in the form of a tube. The porous hydrogel tube comprises a lumen to promote directional cell regeneration, for example. The diameter of the lumen is not particularly limiting. For example, the diameter of the lumen can be in a range of about 50 microns to about 500 microns, about 50 microns to about 400 microns, about 50 microns to about 300 microns, about 50 microns to about 250 microns, about 75 microns to about 400 microns, about 75 microns to about 300 microns, about 75 microns to about 250 microns, about 100 microns to about 300 microns, about 100 microns to about 400 microns, about 100 microns to about 500 microns, about 125 micron to about 275 micron, about 150 microns to about 250 microns, about 150 microns to about 300 microns, about 150 microns to about 400 microns, about 150 microns to about 500 microns, about 250 microns to about 400 microns, about 250 microns to about 500 microns, or about 300 microns to about 500 microns. The diameter of the lumen can advantageously be selected based on the desired end use of the porous hydrogel tube. For example, a porous hydrogel tube having a lumen diameter in a range of about 125 micron to about 275 micron, or about 150 micron to about 250 micron is advantageously provided as a resolution that a cell can detect and is suitable for spinal cord cell regeneration. As a further example, a porous hydrogel tube having a larger lumen diameter, for example in a range of about 300 microns to about 500 microns, can advantageously be used in a vascular graft.

The porous hydrogel tubes of the disclosure, in particular, and the secondary or tertiary structures of the disclosure, in general, can integrate into the surrounding tissue when placed in an injury site. In particular, upon implantation, the lumen of the porous hydrogel tube can fill with blood which carries and deposits proteins into the porous hydrogel tube. The proteins in turn interact with the host tissue to integrate the porous tube into the host. The integration process can be facilitated by using fibrin gel to hold the tube in place during surgery which will be remodeled after a few days by infiltrating cells. Additionally or alternatively, to facilitate integration proteins can be incorporated into the porous hydrogel tubes that will recruit cells more readily from the host to expedite the integration process.

The porous hydrogel tubes and secondary/tertiary structures can further include one or more secondary components. Secondary components can be included to facilitate cross-linking, facilitate integration of the structure with a host tissue, support cell infiltration and tissue regeneration, promote controlled release of therapeutic agents, and/or reduce inflammation of an injury site. Therapeutic agents that can be released from the hydrogel structures can include, but are not limited to, pharmaceutical agents, growth factors, cytokines, and matrix proteins or proteoglycans. Secondary components for facilitating cross-linking can include, but are not limited to, calcium chloride, peptides and/or photoinitiators. Secondary components for facilitating integration with a host tissue can include, but are not limited to, proteins or peptides with non-specific cell adhesion sequences (e.g., RGD, KQAGDV(SEQ ID NO: 1), VAPG(SEQ ID NO: 2)) or with tissue-specific sequences (e.g., neural cell adhesion molecule: YSFNYDGSELIIK-KVDKSDE (SEQ ID NO: 3), ASKKPKRNIKA (SEQ ID NO: 4)) or growth promoting proteins (e.g. soluble growth factors and cytokines) that increase integrin or cell adhesion molecule expression, such as β1. Secondary components for reducing inflammation of an injury site can include, but are not limited to, anti-inflammatory proteins, such as IL-10, IL-4, IL-33, G-CSF, M-CSF, chABC, shortened peptides conjugated to the hydrogel material that can be released as plasmin sensitive peptides degrade. Additionally, as macrophages, microglia, and astrocytes exhibit a pro-inflammatory phenotype and anti-inflammatory phenotype, the tubes can comprise macrophases, microglia, and/or astrocytes to target and shift astrocyte phenotypes to promote regeneration.

In embodiments, the porous hydrogel tube can be configured for placement directly into an injury site. A porous hydrogel tube is configured for placement directly into an injury site when the tube is biocompatible/non-toxic, cut (or able to be cut) to the size of the defect, and the lumen or channel is present and open from one end of the tube to the other. In embodiments wherein a photoinitiator is included in the hydrogel to facilitate cross-linking, the resulting structure can be washed thoroughly to remove the photoinitiator or the photoinitiator may be exchanged for a more biologically inert prior to implementation in the injury site. The hydrogel structure can also have sufficient mechanical integrity to allow placement into the injury site without breaking down. In some embodiments, the hydrogel structure is sufficiently stiff to allow handling when hydrated. In some embodiments, the hydrogel structure may not be sufficiently stiff in the hydrated form to allow handling. Accordingly, the hydrogel structure can be dehydrated, placed into the injury site, and allowed to rehydrate.

Another aspect of the disclosure provides a scaffold for tissue repair, comprising two or more porous hydrogel tubes according to the disclosure. In embodiments, the two or more porous hydrogel tubes are placed on, or are directly adjacent to, one another to form an organized scaffold structure. In embodiments, the two or more porous hydrogel tubes are cross-linked to each other to form a tertiary structure. The cross-linking of the two or more porous hydrogel tubes can be achieved using any of the cross-linking methods described herein as well as other methods known in the art.

Advantageously, the porous hydrogel tubes do not deform (collapse) upon compression, e.g., during cutting, but rather spring back to the original configuration, allowing the porous hydrogel tubes to be cut to various lengths to conform to the dimensions of an injury site.

Example Methods of Use

In general, the organized hydrogel structures of the disclosure can be used as guidance structures for tissue repair, fill and guide repairs for large tissue defects, and/or as guidance conduits for nerve, cardiovascular, musculoskeletal, and other uniaxially aligned tissues. In embodiments, the disclosure provides a method of regenerating tissue comprising implanting in an injury site an implant comprising one or more hydrogel tubes according to the disclosure. In embodiments, the disclosure provides a method of regenerating tissue comprising implanting in an injury site an implant comprising two or more porous hydrogel tubes according to the disclosure, wherein the hydrogel tubes are aligned and stacked within the injury site. In embodiments, the two or more porous hydrogel tubes are cross-linked to each other to form a tertiary structure. In embodiments, the implant comprises a number of hydrogel tubes sufficient to fill the injury site. In embodiments, the implant comprises a secondary or tertiary structure as disclosed herein at a size sufficient to fill the injury site. Advantageously, an implant comprising a plurality of tubes that can be cut to any size and packed to fill any injury shape, offers all the benefits of a hydrogel for wound repair with the direction alignment advantageous for guided tissue repair.

In embodiments, the implant is provided to an injury site within the nervous system, e.g., a spinal cord, or within the vascular system to promote tissue/cell growth, including, but not limited to, axon growth, nerve growth, and/or muscle growth or regeneration.

The implant can be provided in the injury site for a time sufficient to achieve cell growth within the implant. Typically, the implant will remain in the injury site for at least one week, at least 2 weeks, at least 3 weeks, at least 4 weeks, at least 5 weeks, at least 6 weeks, at least 7 weeks, or at least 8 weeks before the hydrogel degrade and up to about 8 weeks, up to about 9 weeks, up to about 10 weeks, up to about 11 weeks, up to about 12 weeks, up to about 13 weeks, up to about 14 weeks, up to about 15 weeks, or up to about 16 weeks.

The implant or the porous hydrogel tube(s) thereof can be injected with a stem cell or a plurality of stem cells. Stem cells can be injected into the implant/hydrogel tube prior to implantation, at the time of implantation, or post-implantation. In embodiments, stem cells can be injected into the implant/hydrogel tube at the time of implantation. In embodiments, stem cells can be injected into the implant/hydrogel tube at the time that the implant/hydrogel tube is being implanted. In embodiments, stem cells can injected into the implant/hydrogel post-implantation, for example, in a range between 1 day and 12 weeks after implantation, between 1 week and 6 weeks after implantation, between 2 weeks and 4 weeks after implantation, for example, 1 day, 2 days, 3 days, 4 days, 5 days, 6 days, 7 days, 8 days, 9 days, 10 days, 11 days, 12 days, 13 days, 14 days, 18 days, 3 weeks, 4 weeks, 5 weeks, 6 weeks, 8 weeks, 10 weeks, or 12 weeks after implantation.

The implant or the porous hydrogel tube(s) thereof can also be used to administer gene therapies and/or biochemical factors, including but not limited to, growth factors, chemokines, aptamers, glycosaminoglycans, and matrix proteins. For example, a gene delivery vector and/or biochemical factor can be incorporated into a hydrogel tube, added on to a hydrogel tube at the time of implantation, or can be administered after implantation of the hydrogel tube to induce a desired change at the injury site. Suitable gene delivery vectors are well known in the art and can include, but are not limited to lentiviruses, retroviruses, adenoviruses, adeno-associated viruses, herpes viruses, pox viruses, alphaviruses, rabies virus and combination thereof. In embodiments, the gene delivery vector can be a lentivirus. Inclusion of a lentivirus can advantageously lead to an overexpression of IL-10 that in turn reduces inflammation at the injury site, thus leading to better stem cell survival when stem cells are provided at the site of the injury.

The implant can be prepared prior to the time of implantation (e.g., prior to surgery) and/or at the time of implantation (e.g., during the surgery at the injury site). For example, porous hydrogel tubes can be prepared prior to the time of implantation. If the size and shape of the injury is known in advance of the implantation, the porous hydrogel tubes can be cut and cross-linked to formed a secondary structure that will be later implanted into the injury site or a mold can be formed to match the injury dimensions, and hydrogel particles filled into the mold and cross-linked to form an organized porous hydrogel implant. If the size and shape of the injury is unknown, the prepared hydrogel tubes can be cut and cross-linked at the site of implantation to provide a secondary structure implant having a shape and size to fill the injury site. For example, lengths of tubes can be loaded into syringes from the extrusion/printing platform, and subsequently, the syringes could be used to dispense and cut the tubes to size directly in the injury site. As a further example, if the hydrogel tubes are dehydrated prior to placement in the injury site, the hydrogel tubes can advantageously be cut prior to dehydration, such that when the tubes rehydrate in the injury site the tubes will not swell to a size greater than the injury site. Swelling of the tubes to a size greater than the injury site would lead to undesirable compression on the surrounding tissue, leading to further injury. Computer controlled fabrication and syringe loading procedures can be used to expand the size and mechanical property restraints to provide more complex geometries. Accordingly, in some embodiments, the implant is formed in a modular fashion at the time and site of implantation.

The implant can also be prepared wholly at the time and site of implantation. For example, at the time of surgery the size and shape of the injury can be determined, followed by extrusion of a plurality of hydrogel particles into a tubular shape, cutting the tubular shape into individual tubes at the desired locations, and and stacking and cross-linking the individual tubes to fill the injury site. Modular formation can be advantageous when the shape or size of the injury is unknown because the number of tubes used can be modified to it the injury and tubes having a variety of lengths can be included. With a large bridge structure, there are fewer degrees of freedom to conform to the injury. In embodiments, the plurality of hydrogel particles are prepared prior to the time of implantation. In alternative embodiments, the plurality of hydrogel particles are prepared at the time of implantation prior to extrusion. Injection or extrusion of fully swelled tubes into the injury can be advantageous as it reduces the likelihood of over-swelling of the tubes and further injury that may result from compression of the tissue and/or allows softer hydrogel materials to be used as the hydrogel tubes would not need to be mechanically strong enough to be handled prior to implantation.

In embodiments wherein the hydrogel particles or porous hydrogel tubes are prepared prior to the time of implantation and a secondary or tertiary structure is formed at the time of implantation, it can be advantageous to prepare the hydrogel particles or porous hydrogel tubes within 24 hours of forming the secondary or tertiary structures, for example, within 18 hours, within 16 hours, within 14 hours, within 12 hours, within 10 hours, within 8 hours, within 6 hours, within 4 hours, or within 2 hours of forming the secondary or tertiary structures to reduce the likelihood of the reactive side arms hydrolyzing and preventing the second phase of polymerization. Additionally, residual liquid should be completely removed from the hydrogel structures. Residual liquid in the hydrogel structures can result in too large of distances between the individual hydrogel particles, thereby weakening or preventing cross-linking.

Specifically contemplated embodiments are set forth in the following table:

| Hydrogel Material | Microsphere Cross-linking Phase | Tube/Larger structure Cross-linking Phase |
|---|---|---|
| PEG-MAL (4 or 8 arm) | Michael Type addition with Plasmin sensitive peptide (e.g., YKND(SEQ ID NO: 5), YKNS(SEQ ID NO: 6), YKNR(SEQ ID NO: 7)) | Photoinitiator & UV/VIS light |
| PEG-MAL (4 or 8 arm) | Michael Type addition with MMP sensitive peptide (e.g., GKCDGPQGYIWGQDCKG (SEQ ID NO: 8)) | Photoinitiator & UV/VIS light |
| PEG-VS (4 or 8 arm) | Michael Type addition with Plasmin sensitive peptide (e.g., YKND(SEQ ID NO: 5), YKNS(SEQ ID NO: 6), YKNR(SEQ ID NO: 7)) | Photoinitiator & UV/VIS light |
| PEG-VS (4 or 8 arm) | Michael Type addition with MMP sensitive peptide (e.g., GKCDGPQGYIWGQDCKG (SEQ ID NO: 8)) | Photoinitiator & UV/VIS light |
| PEG-Ac (4 or 8 arm) + 2% alginate | CaCl2 cross-linking of alginate spheres | Photoinitiator & UV/VIS light to cross-link residual PEG in alginate spheres |
| Alginate & Collagen | CaCl2 cross-linking of alginate spheres | Glutaraldehyde cross-linking of collagen |
| Pluronics (e.g. Pluronic F127) | Self assembles at 37° C. into spheres | Photoinitiator & UV/VIS light or chemical cross-linking |
| Tri-block polymers (e.g. PLGA-PEG-PLGA) | Self assembles at 37° C. into spheres | Photoinitiator & UV/VIS light or chemical cross-linking |

As used herein, the term "about" means within 20%, preferably within 10%, and more preferably within 5% of the stated value.

As used in this specification and the appended claims, the singular forms "a", "an", and "the" include plural references unless the context clearly dictates otherwise.

All publications mentioned herein are incorporated herein by reference in their entirety.

Fabrication and Use of Hydrogel Tube System for Axon Growth

A system of hydrogel tubes was fabricated through a dual phase polymerization process. The system was validated using a mouse spinal cord hemisection injury model and shown to meet the critical need to conform to the injury while guiding axon elongation through the injury. It was found that tubes resulted in a modest increase in immune cell infiltration at 1 week, but this increase was resolved by 2 weeks post injury compared to a no treatment control. Glial scar thickness was significantly reduced in mice that received tube implants and resulted in robust axon growth along the inner and outer surface of the tubes. Axon density within the hydrogel tubes (2087 axons/mm$^2$) was significantly increased compared to the control (250 axons/mm$^2$) or previously reported poly(lactide-co-glycolide) (PLG) bridges (440 axons/mm$^2$) with approximately 30% of all axons myelinated. By comparison, 40-60% of healthy spinal cord axons are myelinated.

Fabrication of PEG Microspheres, Tubes, and Bridges

Fabrication of a modular tube system and multi-channel bridge was generated using a 2-phase polymerization technique adapted from Griffin et. al, Accelerated wound healing by injectable microporous gel scaffolds assembled from annealed building blocks. *Nat Mater.* 2015; 14:737-44. PEG microspheres were first generated using a water/oil emulsion particle fabrication method. 8-arm PEG maleimide (PEG-MAL, 20 kDa; JenKem, Plano, TX) in HEPES (pH 8.0), achieving a final concentration of 20% w/v PEG, was homogenized at 4000 rpm for 30 seconds in 2% Tween-20 (Sigma, St. Louis, MO) in silicone oil (Fisher, Hampton, NH). 5 mM slow degrading plasmin sensitive cross-linking peptide (Ac-GCYKNDGCYKNDCG (SEQ ID NO: 10); Genscript, Piscataway, NJ) in HEPES was added to the PEG-oil mix and homogenized for an additional 60 seconds. The resulting solution was diluted with methanol and diH$_2$O then centrifuged at 10,000 g for 5 minutes. The solution was decanted then rinsed and centrifuged once each with 1% Tween-20 in diH$_2$O and diH$_2$O alone. Microspheres were used to generate tubes and bridges on the same day to ensure that maleimide functional groups did not hydrolyze and could undergo a second phase of polymerization.

Remaining functional groups within the PEG microspheres were cross-linked via free radical polymerization to form the tubes and bridges. Irgacure 2959 photoinitiator (Sigma) dissolved in N-vinylpyrrolidone (660 mg/mL; Sigma) was added to the microspheres at a final concentration of 1% w/v. The resulting microspheres were then packed into either polydimethylsiloxane (PDMS, Dow Corning, Midland, MI) molds to generate tubes or 3D-printed acrylic molds to generate bridges and exposed to an ultraviolet lamp for 3 minutes to initiate free radical polymerization. The cross-linked structures were immediately chilled to −20° C. for 5 minutes, then gently removed from their respective molds. Tubes and bridges were rinsed in PBS (Gibco, Grand Island, NY) for 1 hour at room temperature to ensure removal of excess photoinitiator. Tubes were cut to the length of the bridge molds and 5 were packed into each mold. Tubes were placed in molds to control for size and shape when compared directly to the PEG bridges to avoid potential bias. A solution of 2 mg/mL fibrinogen (Millipore, Billerica, MA), 5 U/mL thrombin (Sigma), and 2.5 mM CaCl$_2$ (Sigma) in tris buffered saline (TBS; Sigma) was added to the molds with the PEG tubes. The molds were incubated for 10 minutes at 37° C. to allow the fibrin solution to gel and secure the tubes into a hydrogel composite. Bridges and tube composites were cut to final lengths of 2 mm, sterilized with 70% ethanol for 60 seconds, then stored at −80° C. until implantation. Throughout the fabrication process the microspheres, tubes, bridges, and tube composites were evaluated under light microscopy to evaluate dimensions and the presence of open channels.

Evaluation of Microspheres, Tubes, and Bridges

Microspheres were suspended in MilliQ water and evaluated with a Mastersizer 2000 (Malvern Instruments, UK) to evaluate size distribution. Porosity was assessed using both weight ratios and scanning electron microscopy. Tubes and bridges were dried in lyophilizer then sputter-coated with gold (SPI Supplies) then analyzed by scanning electron microscope (FEI, Quanta 200 3D). Acquisition conditions were 10 kV, 1.7 nA, 15 mm distance. Resulting images were converted to binary and the percent porosity was averaged across 6 samples. Porosity was confirmed by weighing hydrated materials, lyophilizing and re-weighing to get an estimate of the volume that was attributed to the PEG relative to the void space filled by water.

Surgical Implantation of PEG Structures

All animal work was performed with prior approval and in accordance with the Animal Care and use Committee guidelines at the University of Michigan. A T9-10 lateral hemisection spinal cord injury was created in adult C57BL/6J female mice aged 6-8 weeks, as previously described in Margul et al., Reducing neuroinflammation by delivery of IL-10 encoding lentivirus from multiple-channel bridges. *Bioeng Transl Med.* 2016; 1:136-48. Briefly, the mice were anesthetized with 2% isoflurane and provided preemptive pain management (1 mg kg$^{-1}$ bupivacaine). After confirmation of sufficient anesthesia, a 2 cm incision was made in the skin between the scapula and a laminectomy was performed between T9-10. A 2 mm lateral hemisection was excised and then PEG bridges or PEG tube composites were implanted into the injury site. Gelfoam was used to secure the injury site after which the muscles were sutured and skin stapled. A subset of mice did not receive an implant but did receive gelfoam over the injured spinal cord. Mice were immediately provided post-operative antibiotics (enrofloxacin 2.5 mg kg$^{-1}$ once a day for 2 weeks), analgesics (0.1 mg kg$^{-1}$ buprenorphine twice a day for 3 days), and supportive hydration (1 mL 20 g$^{-1}$ lactated ringer solution once a day for 5 days). Bladders were expressed twice daily until function recovered and staples were removed after 10 days. Mice were euthanized and spinal cord segments (T8-11) were collected after 1, 2, or 8 weeks.

Immunohistochemistry

Isolated spinal cords were flash frozen then cryosectioned transversely (8 week tissue) or longitudinally (2 week tissue) in 18 μm sections. Samples were fixed, permeabilized as necessary, and incubated overnight at 4° C. with primary antibodies. The following antibodies were used for primary detection: rat anti-F4/80 (1:200, Abcam, Cambridge, United Kingdom), goat anti-arginase (1:100, Santa Cruz, Dallas, TX, USA), rabbit anti-neurofilament-200 (1:200, Sigma), goat anti-myelin basic protein (MBP; 1:500, Santa Cruz), chicken anti-P0 (1:250, Ayes Labs). Species-specific secondary antibodies were used for detection at 1:1000 (Life Technologies, Carlsbad, CA, USA). Hoescht 33342 (Life Technologies) was used as a counterstain in all tissue sections. Immunostained tissue sections were imaged using an AxioObserver inverted fluorescent microscope (Zeiss) using a 10× dry objective.

Semi-automated counting software previously described by McCreedy et al., (Semi-automated counting of axon regeneration in poly(lactide co-glycolide) spinal cord bridges. *J Neurosci Methods*, 2016; 263:15-22) was used to quantify axons and the co-localization of myelin with axons in transverse sections taken from the rostral, middle, and caudal regions of the injury. Briefly, the software is calibrated using manual NF-200$^+$ and NF-200$^+$MBP$^+$ counts from a subset of transverse images taken from different animals and regions of the implant. The software then uses a series of Hessian filters and threshold functions within the bridge region to reduce noise for selected NF-200 and MBP images. The software outputs total axon counts, as well as the myelinated axon counts based on the curviliniear MBP co-localizing with axons. ImageJ (NIH, Bethesda, MD, USA) was used to analyze all other fluorescent images and define the bridge area. Cells positive for F4/80$^+$ (macrophages) and F4/80$^+$arginase$^+$ (M2 macrophages) containing Hoescht$^+$ nuclei were counted manually by two blinded researchers to quantify macrophage infiltration.

Flow Cytometry

Spinal cords isolated 1 week after injury and implantation were collected with the bridge and contralateral, but not rostral or caudal tissue to limit myelin debris. Tissue was digested with 1 U mL$^{-1}$ liberase at 37° C. for 6 minutes in thermomixer (Thermo Scientific) at 1400 RPM. Live cells were detected with a blue fix exclusion dye for 15 minutes at 4° C. Cells were then incubated for an additional 30 minutes with Ly6G (PE, 1:1000, Biolegend), arginase (FITC, 1:1000, Abcam), CD4 (PECy7, 1:1000, Biolegend), F4/80 (Alexafluor 700, 1:1000, Biolegend), CD11c (PacBlue, 1:1000, Biolegend), GFAP (APC, 1:1000, BD), CD45 (brilliant violet 510, 1:1000, Biolegend). Cells were then rinsed, fixed with 4% paraformaldehyde for 10 minutes, and rinsed twice more. Samples were analyzed on a MoFlo Astrios flow cytometer using appropriate excitation lasers and emission filters (Beckman Coulter, Brea, CA, USA). Data was analyzed with FlowJo software (FlowJo, Ashland, OR, USA).

Statistics

Multiple comparisons pairs were analyzed using a one-way or two-way ANOVA with Tukey post-hoc test. Significance was defined at a level of $p<0.05$ unless otherwise noted. All values are reported as mean+/−standard deviation.

Hydrogel Porosity and Structure are Controlled Through Dual Phase Cross-Linking of PEG-MAL In the first cross-linking phase: using a water-oil emulsion, a subset of the thiol groups on 8-arm PEG-MAL were cross-linked via Michael-type addition with a repeating YKND(SEQ ID NO: 5) peptide (which is a slow-degrading plasmin sensitive peptide) to form PEG microspheres (FIG. 1A, scale bar 100 micron). The resulting PEG microsphere diameters ranged from 20-80 μm with an average diameter of 45 μm (FIG. 1B).

As several of the maleimide side chains were not used to form the microspheres, secondary and tertiary structures, such as bridges or tubes, could be generated through a second or even third cross-linking phase of these extra maleimide side chains, for example, using UV-sensitive I2959 photoinitiator to form tubes that can subsequently be formed into a bridge composite using fibrin hydrogel to hold the tubes together for implantation (FIG. 1C). Using multiple cross-linking phases allows for the microspheres to contribute porosity that facilitates tissue integration and allows for geometric control of the final structure to support uniaxial regeneration.

In the second cross-linking phase: microspheres were mixed with photoinitiator, cast in molds using pins to create a material void for channels, and exposed to ultraviolet light to initiate free radical-mediated polymerization. In this manner, tertiary structures such as porous tubes and bridges were formed via the cross-linking of the microspheres, where the spaces that had existed between the microspheres formed the pores as the microspheres polymerized together. Porous tube and bridge macrostructures generated from the PEG-MAL microspheres containing aligned channels within the material were confirmed with light microscopy (FIG. 2A-B, scale bar 100 micron), while similar pore size and distribution were observed between the two structures using SEM (FIG. 2C-D). Differences in channel size and overall shape did not contribute to significant differences in porosity and water content for tube composites and bridges (FIG. 2E).

Dual phase cross-linking using an intermediate microspheres phase resulted in a compressive modulus of 12.5 kPa (FIG. 2F, YKND(SEQ ID NO: 5)/PI μs), which is within range of the modulus of the healthy spinal cord (1-300 kPa). Conversely, dual phase cross-linking without an intermediate microsphere phase resulted in a 10-fold increase in modulus (YKND(SEQ ID NO: 5)/PI) and a 100-fold increase was observed when the photoinitiator was used alone (PI only) to cross-link the PEG-MAL (FIG. 2F). The increase in modulus is likely due to a reduction in porosity and would not be reasonable material properties for use in the spinal cord.

PEG Scaffolds Lead to a Modest Increase in Immune Cell Infiltration

Mice that underwent a T9-10 lateral spinal cord hemisection received a 5 tube composite scaffold or a 5 channel PEG bridge (FIG. 3A-B). The PEG bridge served as a control for the previously implemented PLG bridges while tubes were placed in molds to control for size and shape when compared directly to the PEG bridges. A third cohort of mice did not receive any treatment, other than the gelfoam that was used to stabilize the surgical site in all conditions. The injury site and contralateral tissue was isolated after 1 week to evaluate cell infiltration using flow cytometry. As the PEG implants provide a structure for attachment rather than the predominantly void tissue in the control sample, it would be expected that there would be differences in cell infiltration. Interestingly, no differences were observed in the percentage of GFAP$^+$ astrocyte or CD45$^+$ leukocyte at the injury across the blank (gelfoam) or PEG scaffold conditions (FIG. 3C-D). Further evaluation of the distribution of CD45$^+$ leukocyte subtypes did result in significant differences across the conditions. An increase in CD11C$^+$ dendritic cells was observed in both the PEG tubes (32±4%) and bridges (27±3%) compared to the gelfoam control (12±8%; FIG. 3E). Similarly, significantly more F4/80$^+$ macrophages were observed in the PEG tubes (52±7%) compared to the gelfoam control (34±15%), however, no difference in the anti-inflammatory arginaseI$^+$ macrophages were observed. There were no significant differences in the percentage of CD45$^+$ cells expressing Lyg6 neutrophil or CD4 T-cell markers (FIG. 3E). By 2 weeks post-implantation, no significant difference in total, pro-inflammatory M1, or anti-inflammatory M2 macrophage density was observed with histology across conditions (FIG. 7E-G). In FIG. 7, cells nuclei (Hoechst, blue) were observed throughout the tissue for mice receiving gelfoam (FIG. 7A), PEG bridges (FIG. 7B), and PEG tubes (FIG. 7C) with intense staining along the interface of the injured tissue and implants. A subset of these cells F4/80+ macrophages (red), which were quantified as M1 (F4/80+argI−, red, denoted with arrow head) or M2 (F4/80+argI+, red and green, denoted with ">") macrophages when co-localized with nucleus (FIG. 7D).

Glial Scar Formation is Limited by PEG Bridge/Composite Implantation

The glial scar can be observed 2 weeks after spinal cord injury. The glial scar is primarily comprised of astrocytes and provides a physical and biochemical barrier to axon regeneration. Implantation of a scaffold is thought to limit glial scar formation. GFAP+ astrocytes were observed throughout the intact tissue with robust staining at the interface of the gelfoam (FIG. 4A), bridge (FIG. 4B), and tube (FIG. 4C) implants with the intact tissue. Using longitudinal tissue sections, GFAP+ astrocyte thickness at the rostral margin was quantified to approximate the extent and thickness of the physical glial scar. PEG tube composites and bridges significantly reduced glial scar formation to 127±73 µm and 124±44 µm, respectively, compared to the 337±169 µm glial scar thickness in the gelfoam control (FIG. 4D). PEG tubes did not significantly impact glial scarring compared to PEG bridges, suggesting that the tubes achieve comparable apposition to that of the bridge as incomplete apposition would lead to increased inflammation and scarring that would limit regeneration.

Hydrogels with Rostro-Caudal Aligned Channels Increase Axon Elongation

Tube composites were next evaluated for their ability to support and guide axon elongation through the injury compared to the hydrogel bridge and gelfoam control. At 8 weeks after transplantation in T9-10 hemisection, Axons were identified by neurofilament (NF-200+) staining, and transverse tissue sections were separated into three 0.75 mm sections of the implant site: rostral (R), middle (M), and caudal (C) for tissue at 8 weeks (FIG. 5D). NF-200+ axons are present in all sections of bridge in each condition (FIG. 5A-C). Mice receiving tube composites or bridges exhibited the lowest density of axons in the middle of the material while higher axon densities were observed at the rostral and caudal ends of the tubes (FIG. 5D). Conversely, mice that only received the gelfoam control exhibited similar axon densities (456±113 axons/mm$^2$) across all regions of the injury site, likely due to the lack of guidance through the injury (FIG. 5D). A robust increase in axon density was observed in tube composites at the rostral (1744±920 axons/mm$^2$) and caudal (1436±567 axons/mm$^2$) ends when compared to the gelfoam control condition. The hydrogel bridge supported significantly more axon infiltration in the rostral (1048±136 axons/mm$^2$) but not caudal (811±227 axons/mm$^2$) end of the bridge compared to gelfoam controls. The tube composite guides axon growth through the tube channel as well as the exterior tube surface that interfaces with adjacent tubes, in contrast axons are only guided down channels within the bridges. It is likely that the increased cross-sectional area available for axon growth in the tubes compared to the bridge contributed to the differences in axon density between these two conditions as the material properties are comparable. In FIG. 5: data are represented as mean standard deviation, n=6; **$p<0.01$; and the scale bar is 200 micron.

Hydro Gels Support Axon Myelination

The extent of myelinated axons was evaluated to further characterize the extent of tissue regeneration, as healthy axons are myelinated to ensure robust signal propagation. MBP myelin was used to discern total myelinated axons, while P0+ myelin was used to identify myelin from Schwann cells of the peripheral nervous system with P0− myelin being derived from oligodendrocytes native to the central nervous system. Myelinated axons from both oligodendrocytes and Schwann cells were observed in each condition (FIG. 6A). No significant differences were observed in the myelinated axon density (FIG. 6B) or percent of axons myelinated when normalized to axon density (FIG. 6C). Of the myelinated axons, a higher percent of these axons were myelinated by oligodendrocytes in the tube composite (48±19%) and bridge (49±18%) compared 25±16% oligodendrocyte myelinated axons in the predominantly (75±16%) Schwann cell myelinated axons in the gelfoam control (FIG. 6D). In FIG. 6: data are represented as mean standard deviation, n=6; *$p<0.05$; and scale bar is 10 micron.

Behavioral Improvements Following Thoracic Implantation

Figure 10:
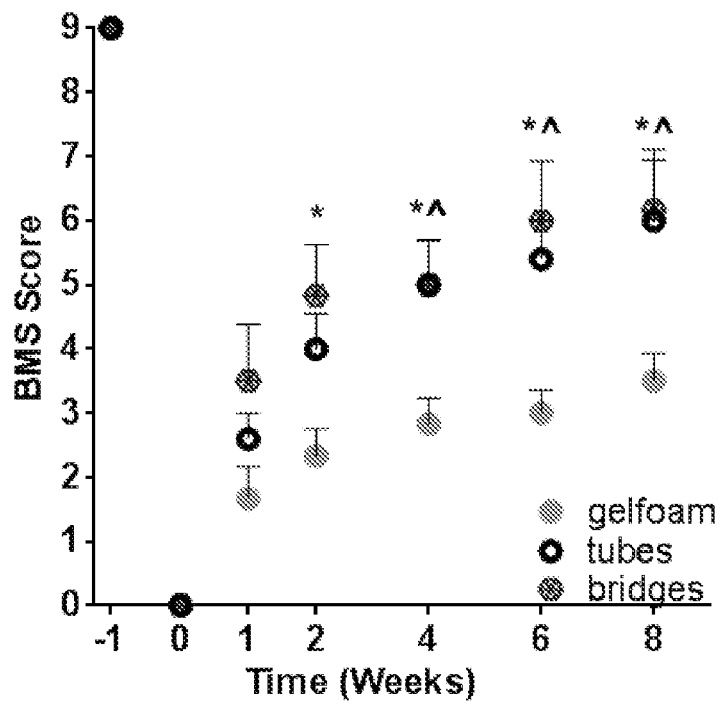
FIG. 10 is a graph of the Basso Mouse Scale score over time for mice implanted with gelfoam, hydrogel tubes, and hydrogel bridges following a thoracic hemisection spinal cord injury.

The Basso Mouse Scale was used to determine improvements in the mice after implantation at 1, 2, 4, 6, and 8 weeks post implantation. The scores are shown in FIG. 10. As shown in FIG. 10, the improvements were significant for the hydrogel bridges compared to gelfoam alone (indicated with *) as early as week 2 and the improvements were significant for the hydrogel tubes compared to gelfoam alone (indicated as ^) as early as week 4.

DISCUSSION

As demonstrated, the modular hydrogel tube system supports and directs uniaxial regeneration following injury and is comparable to a prefabricated hydrogel bridge, both of which surpass the regenerative potential of a no treatment gelfoam control over a large (2.25 mm) spinal cord injury. The improved regenerative capacity of the aligned hydrogels is due, in part, to the channels that guide axons and expedite the repair process, which has been shown extensively with other aligned scaffolds. The increased axon density at 8 weeks in the hydrogels is an improvement over that observed in PLG bridges implanted into a mouse hemisection model, which is likely due to the mechanical properties of the hydrogel tubes and bridges. The system of tubes developed in this work is also an improvement over previous guidance systems as it can be delivered one tube at a time. This modular approach allows the material to conform to any defect size or shape, simply by cutting and stacking the tubes in the defect as necessary. There was no observable difference between cell infiltration, axon extension, or remyelination between the tubes and the preform hydrogel bridges, suggesting this is a feasible approach resulting in good apposition with the intact spinal cord. The system of hydrogel tubes in this work is not limited to applications in spinal cord injury, but could be extended to other tissue engineering problems, such as repair following vascular, musculoskeletal, or peripheral nerve injuries.

With any novel biomaterial, the implications for use are dependent on the ability of the material to remain relatively inert during the inflammatory response initiated after injury. To address this concern, cell infiltration and scar formation was evaluated using a spinal cord injury model. The spinal cord is immune privileged, but following injury, it mounts a robust inflammatory response that leads to further damage and inflammation. Some degree of inflammation is necessary after spinal cord injury in order to clear debris, as studies in which immune cells have been depleted result in worse regenerative and functional outcomes. To further increase the complexity of this model, a glial scar develops after spinal cord injury in an attempt to limit inflammation, but can lead to further damage and inflammation if allowed to persist after the subacute inflammatory phase. Due to the high degree of inflammation following spinal cord injury and the presence of a glial scar, this is a challenging model to deliver a material to without exacerbating the immune response while simultaneously permitting some degree of inflammation and scar formation to occur.

In this study, evaluation of the total immune cell infiltration one week after injury revealed that the PEG materials did not increase immune cell invasion, but elevated macrophages and dendritic cells were observed in the tube composites. By week 2, the macrophage density was similar across all conditions, suggesting that the elevated immune response in the PEG tubes had subsided. At these same time points, the opposite trend was detected with the astrocytes. Using flow cytometry, there were no differences in astrocyte numbers detected at one week, but at week two there were clear morphological differences within astrocytes in the PEG implants. Glial scar formation is more prominent starting at two weeks post injury and is best characterized with histological analysis that is more representative of astrocyte compaction along the injury margin, which is used to quantify scar formation rather than the cell number. In this study, PEG tubes and bridges were able to limit the formation of the glial scar, while the gelfoam control mice presented with thick glial scars. The combined immune cell and astrocyte data suggest that this is a temporally sensitive response that aligns with the timelines reported in the literature. The decrease in scarring and the resolution of the initial macrophage influx supports the robust axon growth through the tube composites and bridges, with the tubes offering the added benefit of increased cross-sectional guidance area compared to the bridges.

PEG is a relatively inert FDA-approved material that passively evades the immune system. Modifications to pore size, cell attachment peptides, and topography could be optimized to further limit inflammation. Moving forward, techniques to shift the immune response could be combined with the tube system to actively reduce inflammation. A reduction in inflammation could be achieved through the inclusion of anti-inflammatory proteins, such as IL-10, IL-4, IL-33, G-CSF, M-CSF, chABC, or preferably shortened peptides could be conjugated to PEG that will be released as the plasmin sensitive peptides degrade. As macrophages, microglia, and astrocytes exhibit a pro-inflammatory phenotype and anti-inflammatory phenotype, similar techniques could be used to target and shift astrocyte phenotypes to promote regeneration.

The inclusion of relevant biochemical factors presents just one way to change the material, and it is an attractive approach when tailoring the biomaterial for tissue-specific application, however, the material could also be modified for each application. For example, the modulus of nervous tissue is relatively low at 1-300 kPA, while the vascular tissue and muscle require high tensile strength. Accordingly, in some embodiments of the present disclosure, alternative polymer backbones are used. In some embodiments, the PEG backbone is replaced with a different polymer backbone appropriate for the injury site. In some embodiments, the maleimide side chains are changed to an alternative composition, such as vinylsulfone. In some embodiments, one or both cross-linking methods are changed to increase the modulus. In some embodiments, the pore size is changed by modifying the microsphere size. Each modification leads to differences in the overall mechanical properties and immune cell infiltration.

For the tubes used in the aforementioned study, there were relatively small scale size restraints to ensure tubes were formed and had sufficient structural stability for handling purposes. This resulted in a smaller pore and reduced porosity compared to the PLG bridges. The PLG bridges are more rigid, and the increased porosity helps to reduce the macroscale mechanical properties.

Hydrogel Tube for Neuro Stem Cell Implantation

All animal work was performed with prior approval and in accordance with the Animal Care and use Committee guidelines at the University of Michigan. A C5 lateral hemisection spinal cord injury was created in C57BL/6 mice aged 14 days. UV linked PEG tube, blank or loaded with lentiviral vectors to deliver an anti-inflammatory factor, interleukin 10 (IL-10), were implanted to fit the injury site using approximately 5 tubes per mouse. A subset of mice did not receive an implant but did receive gelfoam over the injured spinal cord. Dissociated E14 neural stem cells (NSCs) were harvested from the spinal cord of embryonic day 14 (E14) mouse pups in which the isolated cells express enhanced green fluorescent protein (EGFP). After two weeks, harvested NSCs or saline controls were injected directly into the integrated PEG tubes or gelfoam.

Figure 9:
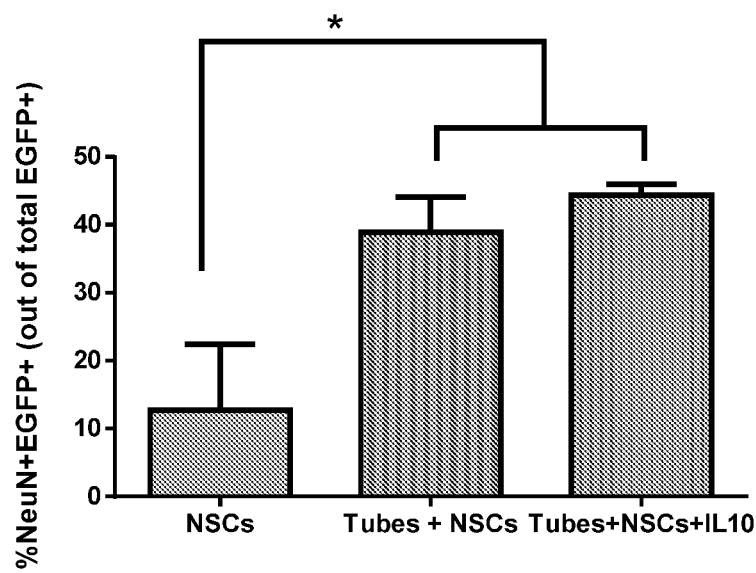
FIG. 9 is a graph comparing the percentage of newly formed neurons arising from transplanted EGFP+ NSCs (reported as % NeuN+ EGFP+) for mice injected with NSCs having no implant, a hydrogel tube implant, or an implant including a hydrogel tube loaded with an anti-inflammatory.

Stem cell survival was evaluated at two weeks after injection of the stem cells, which was 4 weeks after the initial injury. Significantly increased survival was demonstrated for PEG tubes (about 5% survival) and PEG tubes modified with IL-10 (about 10% survival), relative to less than about 1% survival when injected into gelfoam (FIG. 8). By 4 weeks post-implantation, no significant difference in total, pro-inflammatory M1, or anti-inflammatory M2 macrophage density was observed with histology across conditions. The percentage of newly formed NeuN$^+$ neurons from the transplanted EGFP$^+$NSCs at 12 weeks was higher for the PEG tubes relative to the gelfoam (FIG. 9).

Figure 11:
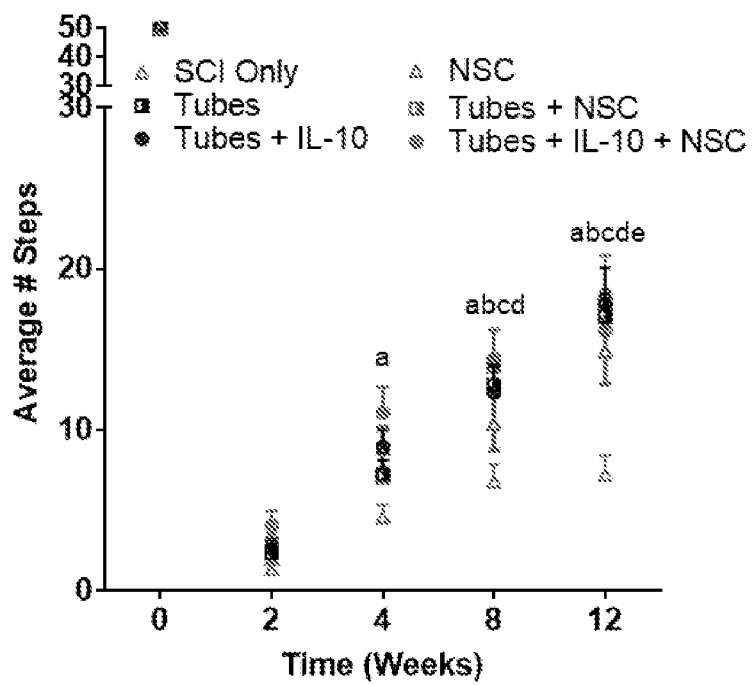
FIG. 11 is a graph of the average number of steps taken on the ladder beam over time for mice implanted with gel foam only, hydrogel tubes only, hydrogel tubes loaded with an anti-inflammatory only, and mice implanted with each of the three foregoing implants and further injected with NSCs in a cervical hemisection spinal cord injury.

The ladder beam was used to determine improvements in the mice after implantation at 2, 4, 8, and 12 weeks post implantation. The average number of steps are shown in FIG. 11. As shown in FIG. 11, the steps taken by mice injected with NSC ("e") were significantly higher from the steps taken by mice with gelfoam alone by 12 weeks; the steps taken by mice including PEG tubes and no NSC ("d"), mice including the PEG tubes and NSC ("c"), mice including PEG tubes loaded with IL-10 and no NSC ("b") were significantly different from the steps taken by mice with gelfoam alone by 8 weeks; and the steps taken by mice PEG tubes loaded with IL-10 and including NSC ("a") were significantly different from the steps taken by mice with gelfoam alone by 4 weeks.

Figure 12:
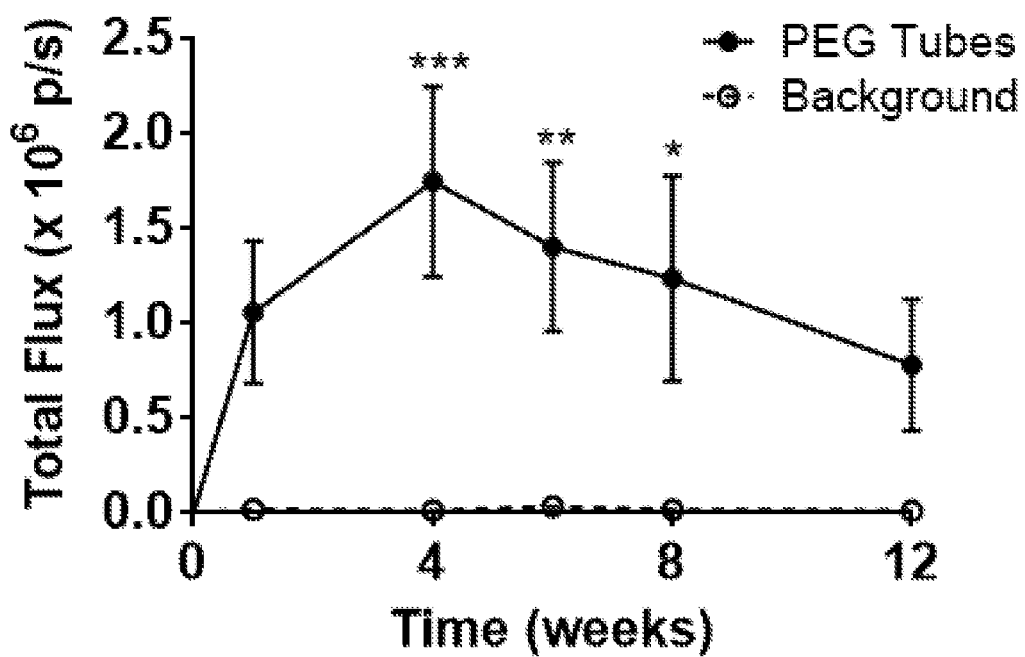
FIG. 12 is a graph showing sustained expression of lentiviral vectors by cells at the injury site for at least 8 weeks.

Sustained expression of lentiviral vectors by cells at the injury site for at least 8 weeks was determined by loading the tubes with a lentivirus that encodes for a firefly luciferase reporter gene (FIG. 12). In vivo bioluminescent imaging was used to detect cells with the firefly luciferase reporter gene by administering d-luciferin prior to imaging. Cells with the firefly luciferase reporter gene were detected up to 8 weeks after injury, demonstrating prolonged gene expression within the injury. Such prolonged gene expression of the firefly luciferase reporter gene confirms that other factors, such as an anti-inflammatory factor, will also advantageously provide prolonged expression at the injury.

Thus, improvements in stem cell survival and recovery were demonstrated using PEG tubes and PEG tubes modified with IL-10, relative to gelfoam alone. Advantageously the hydrogel tubes had a low modulus that was similar to nervous system which created a microenvironment that facilitated stem cell transplantation after initial inflammation had subsided. When coupled with anti-inflammatory therapies, implantation sites that will be more hospitable to delayed stem cell implantation can be created.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention. The foregoing description is given for clearness of understanding; and no unnecessary limitations should be understood therefrom, as modifications within the scope of the invention may be apparent to those having ordinary skill in the art.

REFERENCES

[1] Lee B B, Cripps R A, Fitzharris M, Wing P C. The global map for traumatic spinal cord injury epidemiology: update 2011, global incidence rate. Spinal Cord. 2014; 52:110-6.

[2] Anderson K D, Cowan R E, Horsewell J. Facilitators and Barriers to Spinal Cord Injury Clinical Trial Participation: Multi-National Perspective of People Living with Spinal Cord Injury. J Neurotrauma. 2016; 33:493-9.

[3] Basso D M, Beattie M S, Bresnahan J C. Graded histological and locomotor outcomes after spinal cord contusion using the NYU weight-drop device versus transection. Exp Neurol. 1996; 139:244-56.

[4] McCreedy D A, Margul D J, Seidlits S K, Antane J T, Thomas R J, Sissman G M, et al. Semi-automated counting of axon regeneration in poly(lactide co-glycolide) spinal cord bridges. J Neurosci Methods. 2016; 263:15-22.

[5] Cao H, Liu T, Chew S Y. The application of nanofibrous scaffolds in neural tissue engineering. Adv Drug Deliv Rev. 2009; 61:1055-64.

[6] Madigan N N, McMahon S, O'Brien T, Yaszemski M J, Windebank A J. Current tissue engineering and novel therapeutic approaches to axonal regeneration following spinal cord injury using polymer scaffolds. Respir Physiol Neurobiol. 2009; 169:183-99.

[7] Thomas A M, Kubilius M B, Holland S J, Seidlits S K, Boehler R M, Anderson A J, et al. Channel density and porosity of degradable bridging scaffolds on axon growth after spinal injury. Biomaterials. 2013; 34:2213-20.

[8] Tuinstra H M, Margul D J, Goodman A G, Boehler R M, Holland S J, Zelivyanskaya M L, et al. Long-term characterization of axon regeneration and matrix changes using multiple channel bridges for spinal cord regeneration. Tissue Eng Part A. 2014; 20:1027-37.

[9] Colello R J, Chow W N, Bigbee J W, Lin C, Dalton D, Brown D, et al. The incorporation of growth factor and chondroitinase ABC into an electrospun scaffold to promote axon regrowth following spinal cord injury. J Tissue Eng Regen Med. 2013.

[10] Tsai E C, Dalton P D, Shoichet M S, Tator C H. Matrix inclusion within synthetic hydrogel guidance channels improves specific supraspinal and local axonal regeneration after complete spinal cord transection. Biomaterials. 2006; 27:519-33.

[11] Pawar K, Cummings B J, Thomas A, Shea L D, Levine A, Pfaff S, et al. Biomaterial bridges enable regeneration and re-entry of corticospinal tract axons into the caudal spinal cord after SCI: Association with recovery of forelimb function. Biomaterials. 2015; 65:1-12.

[12] Gunther M I, Weidner N, Muller R, Blesch A. Cell-seeded alginate hydrogel scaffolds promote directed linear axonal regeneration in the injured rat spinal cord. Acta Biomater. 2015; 27:140-50.

[13] Gelain F, Panseri S, Antonini S, Cunha C, Donega M, Lowery J, et al. Transplantation of nanostructured composite scaffolds results in the regeneration of chronically injured spinal cords. ACS Nano. 2011; 5:227-36.

[14] Han S, Wang B, Jin W, Xiao Z, Chen B, Xiao H, et al. The collagen scaffold with collagen binding BDNF enhances functional recovery by facilitating peripheral nerve infiltrating and ingrowth in canine complete spinal cord transection. Spinal Cord. 2014; 52:867-73.

[15] Kubinova S, Horak D, Hejcl A, Plichta Z, Kotek J, Proks V, et al. SIKVAV-modified highly superporous PHEMA scaffolds with oriented pores for spinal cord injury repair. J Tissue Eng Regen Med. 2015; 9:1298-309.

[16] Liu C, Huang Y, Pang M, Yang Y, Li S, Liu L, et al. Tissue-engineered regeneration of completely transected spinal cord using induced neural stem cells and gelatin-electrospun poly(lactide-co-glycolide)/polyethylene glycol scaffolds. PLoS One. 2015; 10:e0117709.

[17] Assuncao-Silva R C, Gomes E D, Sousa N, Silva N A, Salgado A J. Hydrogels and Cell Based Therapies in Spinal Cord Injury Regeneration. Stem Cells Int. 2015; 2015:948040.

[18] Mothe A J, Tam R Y, Zahir T, Tator C H, Shoichet M S. Repair of the injured spinal cord by transplantation of neural stem cells in a hyaluronan-based hydrogel. Biomaterials. 2013; 34:3775-83.

[19] Rajnicek A, Britland S, McCaig C. Contact guidance of CNS neurites on grooved quartz: influence of groove dimensions, neuronal age and cell type. J Cell Sci. 1997; 110 (Pt 23):2905-13.

[20] Miller C, Jeftinija S, Mallapragada S. Synergistic effects of physical and chemical guidance cues on neurite alignment and outgrowth on biodegradable polymer substrates. Tissue Eng. 2002; 8:367-78.

[21] Dumont C M, Munsell, M. K., Carlson, M. A., Cummings, B. J., Anderson, A. J., Shea, L. D. Neural stem cell-laden multichannel bridges support axon regeneration and neurogenesis following spinal cord injury. Submitted.

[22] Hunt M, Lu P, Tuszynski M H. Myelination of axons emerging from neural progenitor grafts after spinal cord injury. Exp Neurol. 2017; 296:69-73.

[23] Chung K, Coggeshall R E. Numbers of axons in lateral and ventral funiculi of rat sacral spinal cord. J Comp Neurol. 1983; 214:72-8.

[24] Chung K, Coggeshall R E. Propriospinal fibers in the rat. J Comp Neurol. 1983; 217:47-53.

[25] Griffin D R, Weaver W M, Scumpia P O, Di Carlo D, Segura T. Accelerated wound healing by injectable microporous gel scaffolds assembled from annealed building blocks. Nat Mater. 2015; 14:737-44.

[26] Shikanov A, Smith R M, Xu M, Woodruff T K, Shea L D. Hydrogel network design using multifunctional macromers to coordinate tissue maturation in ovarian follicle culture. Biomaterials. 2011; 32:2524-31.

[27] Margul D J, Park J, Boehler R M, Smith D R, Johnson M A, McCreedy D A, et al. Reducing neuroinflammation by delivery of IL-10 encoding lentivirus from multiple-channel bridges. Bioeng Transl Med. 2016; 1:136-48.

[28] Karimi A, Shojaei A, Tehrani P. Mechanical properties of the human spinal cord under the compressive loading. J Chem Neuroanat. 2017; 86:15-8.

[29] Oakland R J, Hall R M, Wilcox R K, Barton D C. The biomechanical response of spinal cord tissue to uniaxial loading. Proc Inst Mech Eng H. 2006; 220:489-92.

[30] Ozawa H, Matsumoto T, Ohashi T, Sato M, Kokubun S. Comparison of spinal cord gray matter and white matter softness: measurement by pipette aspiration method. J Neurosurg. 2001; 95:221-4.

[31] Dumont C M, Margul D J, Shea L D. Tissue Engineering Approaches to Modulate the Inflammatory Milieu following Spinal Cord Injury. Cells Tissues Organs. 2016; 202:52-66.

[32] Cregg J M, DePaul M A, Filous A R, Lang B T, Tran A, Silver J. Functional regeneration beyond the glial scar. Exp Neurol. 2014; 253:197-207.

[33] Stirling D P, Liu S, Kubes P, Yong V W. Depletion of Ly6G/Gr-1 leukocytes after spinal cord injury in mice alters wound healing and worsens neurological outcome. J Neurosci. 2009; 29:753-64.

[34] Shechter R, London A, Varol C, Raposo C, Cusimano M, Yovel G, et al. Infiltrating blood-derived macrophages are vital cells playing an anti-inflammatory role in recovery from spinal cord injury in mice. PLoS Med. 2009; 6:e1000113.

[35] Donnelly D J, Popovich P G. Inflammation and its role in neuroprotection, axonal regeneration and functional recovery after spinal cord injury. Exp Neurol. 2008; 209:378-88.

[36] Dumont C M, Park J, Shea L D. Controlled release strategies for modulating immune responses to promote tissue regeneration. J Control Release. 2015; 219:155-66.

[37] Bethea J R, Nagashima H, Acosta M C, Briceno C, Gomez F, Marcillo A E, et al. Systemically administered interleukin-10 reduces tumor necrosis factor-alpha production and significantly improves functional recovery following traumatic spinal cord injury in rats. J Neurotrauma. 1999; 16:851-63.

[38] Vannier E, Miller L C, Dinarello C A. Coordinated antiinflammatory effects of interleukin 4: interleukin 4 suppresses interleukin 1 production but up-regulates gene expression and synthesis of interleukin 1 receptor antagonist. Proc Natl Acad Sci USA. 1992; 89:4076-80.

[39] Lee S I, Jeong S R, Kang Y M, Han D H, Jin B K, Namgung U, et al. Endogenous expression of interleukin-4 regulates macrophage activation and confines cavity formation after traumatic spinal cord injury. J Neurosci Res. 2010; 88:2409-19.

[40] Fenn A M, Hall J C, Gensel J C, Popovich P G, Godbout J P. IL-4 signaling drives a unique arginase+/IL-1beta+ microglia phenotype and recruits macrophages to the inflammatory CNS: consequences of age-related deficits in IL-4Ralpha after traumatic spinal cord injury. J Neurosci. 2014; 34:8904-17.

[41] Pomeshchik Y, Kidin I, Korhonen P, Savchenko E, Jaronen M, Lehtonen S, et al. Interleukin-33 treatment reduces secondary injury and improves functional recovery after contusion spinal cord injury. Brain Behav Immun 2015; 44:68-81.

[42] Guo Y, Zhang H, Yang J, Liu S, Bing L, Gao J, et al. Granulocyte colony-stimulating factor improves alternative activation of microglia under microenvironment of spinal cord injury. Neuroscience. 2013; 238:1-10.

[43] Hamilton T A, Zhao C, Pavicic P G, Jr., Datta S. Myeloid colony-stimulating factors as regulators of macrophage polarization. Front Immunol. 2014; 5:554.

[44] Didangelos A, Iberl M, Vinsland E, Bartus K, Bradbury E J. Regulation of IL-10 by chondroitinase ABC promotes a distinct immune response following spinal cord injury. J Neurosci. 2014; 34:16424-32.

[45] Zisch A H, Lutolf M P, Ehrbar M, Raeber G P, Rizzi S C, Davies N, et al. Cell-demanded release of VEGF from synthetic, biointeractive cell ingrowth matrices for vascularized tissue growth. FASEB J. 2003; 17:2260-2.

[46] Liddelow S A, Guttenplan K A, Clarke L E, Bennett F C, Bohlen C J, Schirmer L, et al. Neurotoxic reactive astrocytes are induced by activated microglia. Nature. 2017; 541:481-7.

---

What is claimed is:

1. A method of regenerating tissue, the method comprising:
implanting in an injury site an implant comprising two or more porous hydrogel tubes wherein the hydrogel tubes each comprise a plurality of crosslinked hydrogel particles comprising a polyethylene glycol-based material, wherein the polyethylene glycol-based material comprises polyethylene glycol having one or more reactive side arms, and wherein the crosslinked polyethylene glycol-based hydrogel particles are cross-linked to each other in the form of a tube, and
wherein the hydrogel tubes are aligned and stacked within the injury site.

2. The method of claim 1, wherein the two or more porous hydrogel tubes fill the injury site.

3. The method of claim 1, wherein the implant remains in the injury site for a period of time up to and including 16 weeks to achieve cell growth within the implant.

4. The method of claim 1, wherein the two or more porous hydrogel tubes are provided as a scaffold.

5. The method of claim 1, wherein the implant remains in the injury site for a period of time up to and including 8 weeks to achieve cell growth within the implant.

6. The method of claim 5, wherein cell growth comprises axon growth.

7. The method of claim 1, wherein the injury site is within a spinal cord.

8. The method of claim 1, wherein the porous hydrogel tube is prepared prior to the time of implantation.

9. The method of claim 1, wherein the one or more reactive side arms comprise maleimide side arms, acrylate side arms, vinyl sulfone side arms, thiol-containing side arms or a combination thereof.

10. The method of claim 9, wherein the one or more reactive side arms comprise maleimide side arms.

11. The method of claim 10, wherein the polyethylene glycol-based material comprises 4-arm polyethylene glycol maleimide, 8-arm polyethylene glycol maleimide or a combination thereof.

12. The method of claim 11, wherein the polyethylene glycol-based material comprises 8-arm polyethylene glycol maleimide.

13. The method of claim 1, wherein the porous hydrogel tubes are hydrated.

14. A method of regenerating tissue, the method comprising:
implanting in an injury site an implant comprising two or more porous hydrogel tubes wherein the hydrogel tubes each comprise a plurality of hydrogel particles cross-linked to each other in the form of a tube,
and wherein the hydrogel tubes are aligned and stacked within the injury site,
and wherein the plurality of hydrogel tubes are formed at the time of implantation by cross-linking a plurality of hydrogel particles,
extruding the resulting hydrogel particles into a tubular shape, and
cutting the tubular shape at the desired locations to achieve porous hydrogel tubes.

15. The method of claim 14, wherein the plurality of hydrogel particles comprise crosslinked hydrogel particles and the crosslinked hydrogel particles comprise a polyethylene glycol-based material.

16. The method of claim 15, wherein the polyethylene glycol-based material comprises polyethylene glycol having one or more reactive side arms.

17. The method of claim 16, wherein the one or more reactive side arms comprise maleimide side arms, acrylate side arms, vinyl sulfone side arms, thiol-containing side arms or a combination thereof.

18. The method of claim 17, wherein the one or more reactive side arms comprise maleimide side arms.

19. The method of claim 18, wherein the polyethylene glycol-based material comprises 4-arm polyethylene glycol maleimide, 8-arm polyethylene glycol maleimide or a combination thereof.

20. The method of claim 19, wherein the polyethylene glycol-based material comprises 8-arm polyethylene glycol maleimide.

* * * * *